United States Patent
Iwase et al.

(10) Patent No.: US 10,846,892 B2
(45) Date of Patent: Nov. 24, 2020

(54) IMAGE PROCESSING APPARATUS, IMAGE PROCESSING METHOD, AND STORAGE MEDIUM

(71) Applicant: CANON KABUSHIKI KAISHA, Tokyo (JP)

(72) Inventors: Yoshihiko Iwase, Yokohama (JP); Hiroki Uchida, Tokyo (JP)

(73) Assignee: CANON KABUSHIKI KAISHA, Tokyo (JP)

(*) Notice: Subject to any disclaimer, the term of this patent is extended or adjusted under 35 U.S.C. 154(b) by 263 days.

(21) Appl. No.: 16/121,429

(22) Filed: Sep. 4, 2018

(65) Prior Publication Data
US 2019/0073805 A1    Mar. 7, 2019

(30) Foreign Application Priority Data
Sep. 7, 2017    (JP) ................. 2017-172335

(51) Int. Cl.
*G06T 11/00* (2006.01)
*A61B 3/10* (2006.01)
(Continued)

(52) U.S. Cl.
CPC .......... *G06T 11/008* (2013.01); *A61B 3/0025* (2013.01); *A61B 3/102* (2013.01);
(Continued)

(58) Field of Classification Search
CPC ......... G06T 11/008; G06T 7/33; G06T 7/337; G06T 7/0016; G06T 7/55;
(Continued)

(56) References Cited

U.S. PATENT DOCUMENTS 10,107,613 B2* 10/2018 Jiao .................... G01N 29/0681
2006/0187462 A1* 8/2006 Srinivasan ............. A61B 3/102
356/479

(Continued)

FOREIGN PATENT DOCUMENTS

JP    5832523 B2    12/2015

*Primary Examiner* — Carol Wang
(74) *Attorney, Agent, or Firm* — Canon U.S.A., Inc. IP Division

(57) ABSTRACT

An apparatus includes: an acquisition unit configured to acquire pieces of three-dimensional data of a subject eye obtained at different times, the three-dimensional data including pieces of two-dimensional data obtained at different positions; a first planar alignment unit configured to perform first planar alignment including alignment between the pieces of three-dimensional data in a plane orthogonal to a depth direction of the subject eye; a first depth alignment unit configured to perform first depth alignment including alignment between pieces of two-dimensional data in at least one piece of three-dimensional data among the pieces of three-dimensional data and further including alignment between the pieces of three-dimensional data in the depth direction; and a generation unit configured to generate interpolation data of at least one piece of three-dimensional data among the pieces of three-dimensional data by using a result of the first planar alignment and a result of the first depth alignment.

15 Claims, 19 Drawing Sheets

(51) Int. Cl.
  *A61B 3/12*  (2006.01)
  *G06T 7/00*  (2017.01)
  *G06T 7/55*  (2017.01)
  *A61B 3/00*  (2006.01)
  *G06T 7/33*  (2017.01)

(52) U.S. Cl.
  CPC .......... *A61B 3/1225* (2013.01); *G06T 7/0016* (2013.01); *G06T 7/33* (2017.01); *G06T 7/337* (2017.01); *G06T 7/55* (2017.01); *G06T 2207/10028* (2013.01); *G06T 2207/10101* (2013.01); *G06T 2207/20201* (2013.01); *G06T 2207/30041* (2013.01)

(58) Field of Classification Search
  CPC . G06T 2207/30041; G06T 2207/10028; G06T 2207/10101; G06T 2207/20201; A61B 3/102; A61B 3/1225; A61B 3/0025
  See application file for complete search history.

(56) References Cited

U.S. PATENT DOCUMENTS

| | | | |
|---|---|---|---|
| 2011/0267340 A1 | 11/2011 | Kraus | |
| 2012/0294500 A1* | 11/2012 | Utsunomiya | A61B 3/1025 382/128 |
| 2015/0335234 A1* | 11/2015 | Okada | A61B 3/0083 351/208 |
| 2017/0131082 A1 | 5/2017 | Cheng | |

* cited by examiner

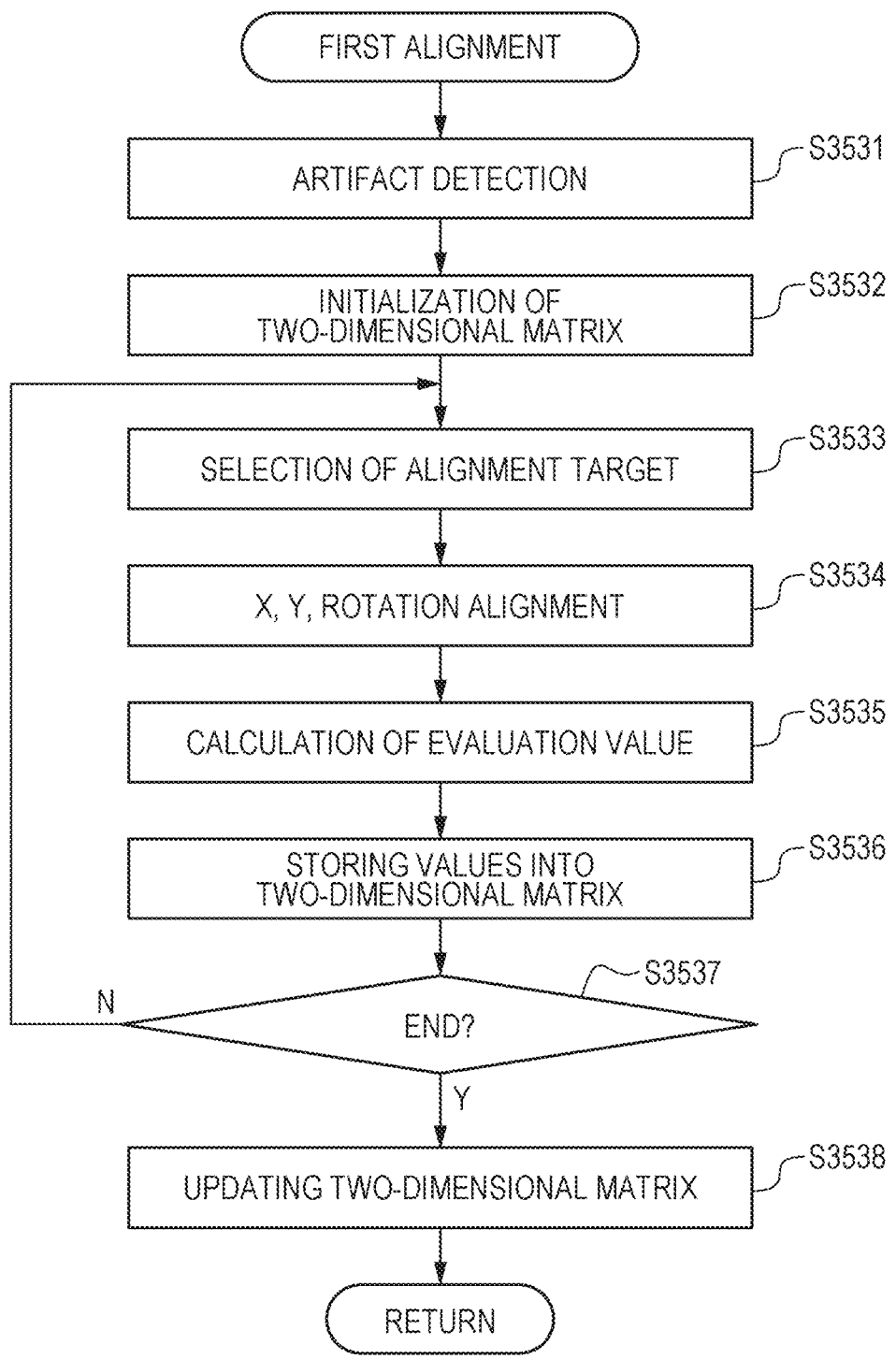

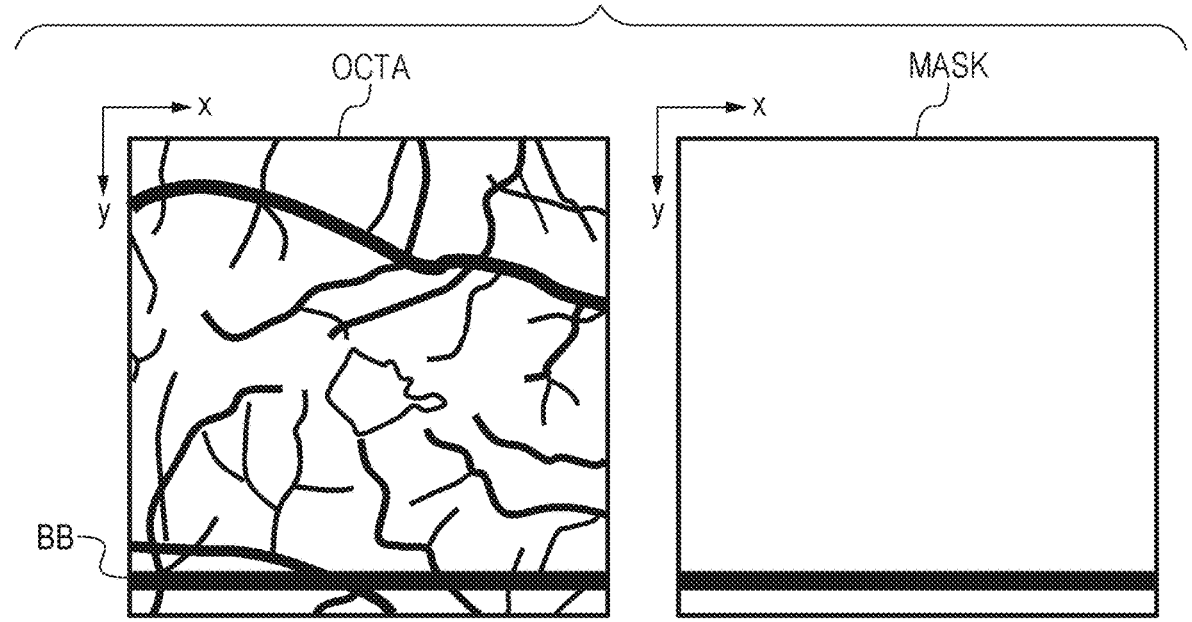
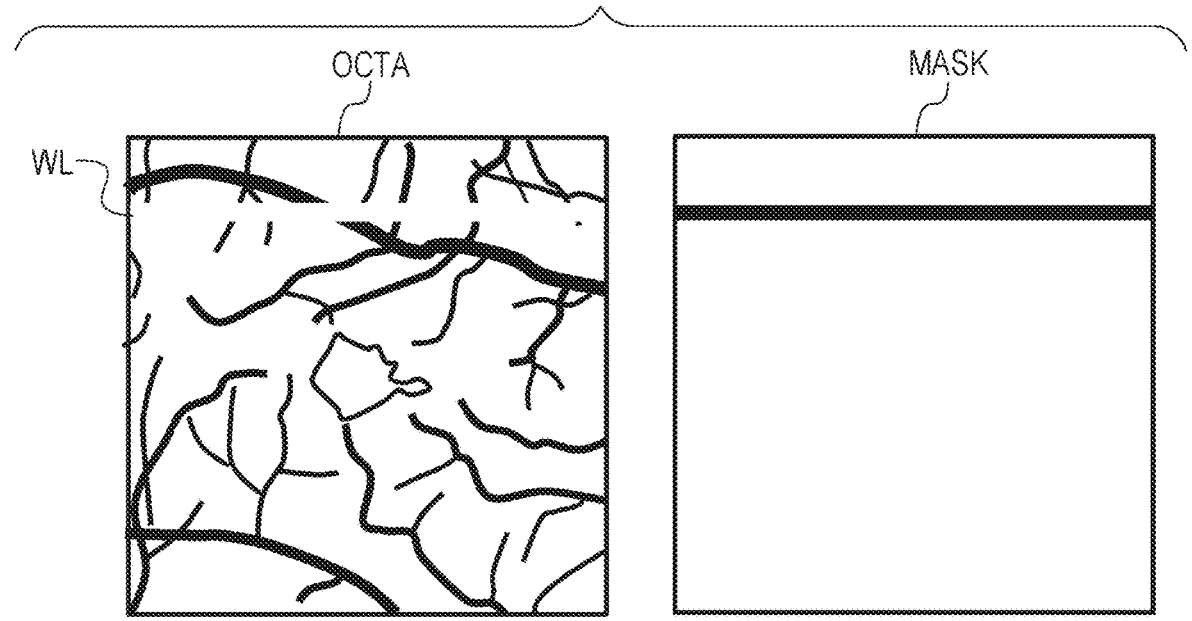

IMAGE PROCESSING APPARATUS, IMAGE PROCESSING METHOD, AND STORAGE MEDIUM

BACKGROUND OF THE INVENTION

Field of the Invention

An embodiment of the disclosed technique relates to an image processing apparatus, an image processing method, and a non-transitory computer-readable storage medium storing a program.

Description of the Related Art

An imaging apparatus for ophthalmic tomography such as optical coherence tomography (OCT) makes it possible to observe the state of the inside of retinal layers of an eye three-dimensionally. Recently, such a tomographic imaging apparatus has attracted attention because it is useful for diagnosing a disease with improved accuracy. For example, SD-OCT (spectral domain OCT), which is a kind of OCT for obtaining an interferogram by a spectrometer using a wideband light source, is known as a method for high-speed image acquisition. In addition, SS-OCT (swept source OCT) based on a method of measuring spectral interference by a single channel photo detector using a high-speed wavelength-sweeping light source is known. Recently, angiography using OCT (OCT Angiography: OCTA) has been proposed as an angiographic method that does not use any radiocontrast agent. In OCTA, a blood vessel image (hereinafter referred to as "OCTA image") is generated by projecting three-dimensional (3D) motion contrast data acquired by OCT onto a two-dimensional (2D) plane. Motion contrast data mentioned here is data of a change detected in a measurement object over time between one imaging and another during repetitive imaging of the same cross section of the measurement object by OCT. For example, motion contrast data is obtained by calculating a change in phase, vector, intensity of a complex OCT signal from difference, ratio, or correlation, etc.

When 3D data of a measurement object is acquired by an OCT apparatus, motion artifacts appear in the data due to movement of the subject eye. To address this problem, a technique of generating 3D data with motion artifact compensation by aligning or merging volume data based on x-directional scanning with volume data based on y-directional scanning is known (Japanese Patent No. 5832523).

SUMMARY OF THE INVENTION

An image processing apparatus disclosed herein includes: an acquisition unit configured to acquire pieces of three-dimensional data of a subject eye obtained at different times, the three-dimensional data including pieces of two-dimensional data obtained at different positions; a first planar alignment unit configured to perform first planar alignment including alignment between the pieces of three-dimensional data in a plane orthogonal to a depth direction of the subject eye; a first depth alignment unit configured to perform first depth alignment including alignment between pieces of two-dimensional data in at least one piece of three-dimensional data among the pieces of three-dimensional data and further including alignment between the pieces of three-dimensional data in the depth direction; and a generation unit configured to generate interpolation data of at least one piece of three-dimensional data among the pieces of three-dimensional data by using a result of the first planar alignment and a result of the first depth alignment.

Further features of the present invention will become apparent from the following description of exemplary embodiments with reference to the attached drawings.

BRIEF DESCRIPTION OF THE DRAWINGS

FIG. 4 is a flowchart that illustrates an example of the flow of first alignment processing.

FIG. 8A is a diagram for explaining an example of artifact removal.

FIG. 8B is a diagram for explaining an example of artifact removal.

DESCRIPTION OF THE EMBODIMENTS

In order to conduct an analysis using pieces of 3D data captured by OCT, it is necessary to improve 3D data alignment accuracy.

The embodiment disclosed below makes it possible to align pieces of 3D data captured by OCT and obtain high-quality 3D data with reduced artifacts.

First Embodiment

With reference to the accompanying drawings, a first embodiment will now be explained. To generate 3D motion contrast data with reduced artifacts, an image processing apparatus according to the present embodiment has features of aligning pieces of motion contrast data and selecting motion contrast data taken as a reference for alignment to perform averaging. The numerical values disclosed in the embodiment below are examples. The scope of the disclosure is not limited to these examples.

With the present embodiment, it is possible to acquire high-quality 3D motion contrast data even in a case where artifacts exist in motion contrast data due to, for example, involuntary eye movements during fixation. In the description herein, "high quality" means an image with an improved S/N ratio as compared with an image based on imaging performed once. Alternatively, "high quality" means an image that has an increased amount of information necessary for making a diagnosis. In the present embodiment, 3D data refers to 3D tomographic image data containing luminance values and 3D motion contrast data containing decorrelation values.

An image processing system that includes an image processing apparatus according to the present embodiment will now be explained in detail.

Figure 1:
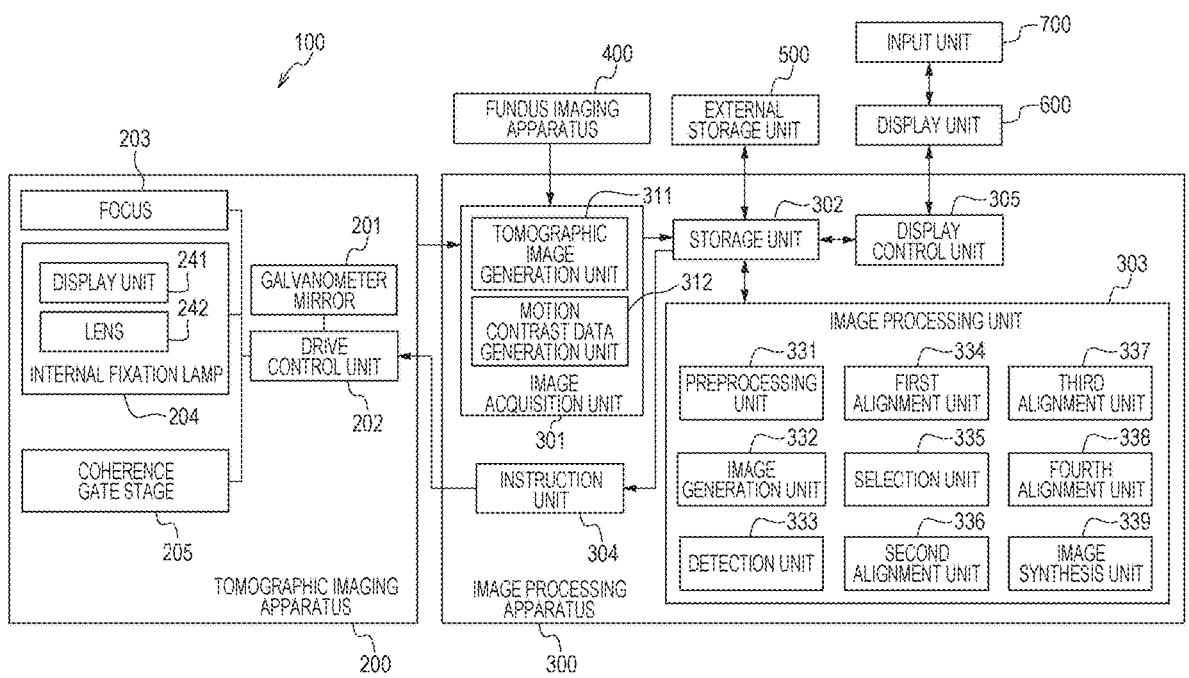
FIG. 1 is a diagram that illustrates an example of the configuration of an image processing system.

FIG. 1 is a diagram that illustrates the configuration of an image processing system 100 that includes an image processing apparatus 300 according to the present embodiment. In the image processing system 100, as illustrated in FIG. 1, the image processing apparatus 300 is connected via interfaces to a tomographic imaging apparatus (referred to also as OCT) 200, a fundus imaging apparatus 400, an external storage unit 500, a display unit 600, and an input unit 700.

The tomographic imaging apparatus 200 is an apparatus that captures a tomographic image of an eye. For example, SD-OCT or SS-OCT is used as the tomographic imaging apparatus. Since the tomographic imaging apparatus 200 is a known apparatus, it is briefly explained, and a detailed explanation is omitted. The description of the tomographic imaging apparatus 200 below is mainly focused on tomographic image capturing performed in response to instructions from the image processing apparatus 300.

In FIG. 1, a galvanometer mirror 201 scans the fundus with measurement light and defines the range of imaging the fundus by OCT. A drive control unit 202 determines the imaging range in a planar direction on the fundus and the number of scanning lines (scan speed in the planar direction). For simplicity, the galvanometer mirror is illustrated as a single unit. However, actually, the galvanometer mirror is made up of two mirrors, one for X scanning and the other for Y scanning, and is capable of scanning a predetermined range on the fundus with measurement light.

A focus 203 is a device for focusing on retinal layers of the fundus through the anterior segment of an eye that is a subject to be examined. Specifically, measurement light is focused on the retinal layers of the fundus by a non-illustrated focus lens through the anterior segment of an eye that is a subject to be examined. Measurement light impinging upon the fundus is reflected and scattered by each retinal layer, and returns.

An internal fixation lamp 204 includes a display unit 241 and a lens 242. As the display unit 241, light emitting diodes (LED) arranged in a matrix are used. The lighting position of the light emitting diodes is changed in accordance with the region that is wanted to be imaged under the control of the drive control unit 202. Light emitted from the display unit 241 is guided to the subject eye through the lens 242. Light emitted from the display unit 241 has a wavelength of 520 nm. A predetermined pattern is displayed under the control of the drive control unit 202.

Figure 2A:
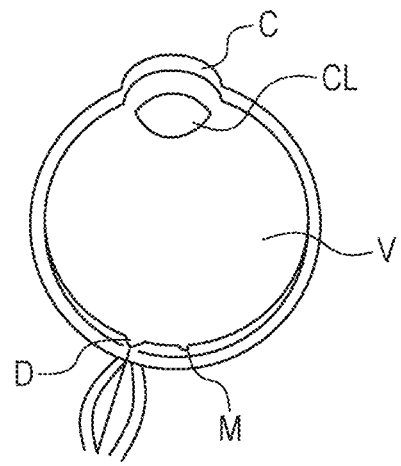
FIG. 2A is a diagram for explaining the structure of an eye.
Figure 2B:
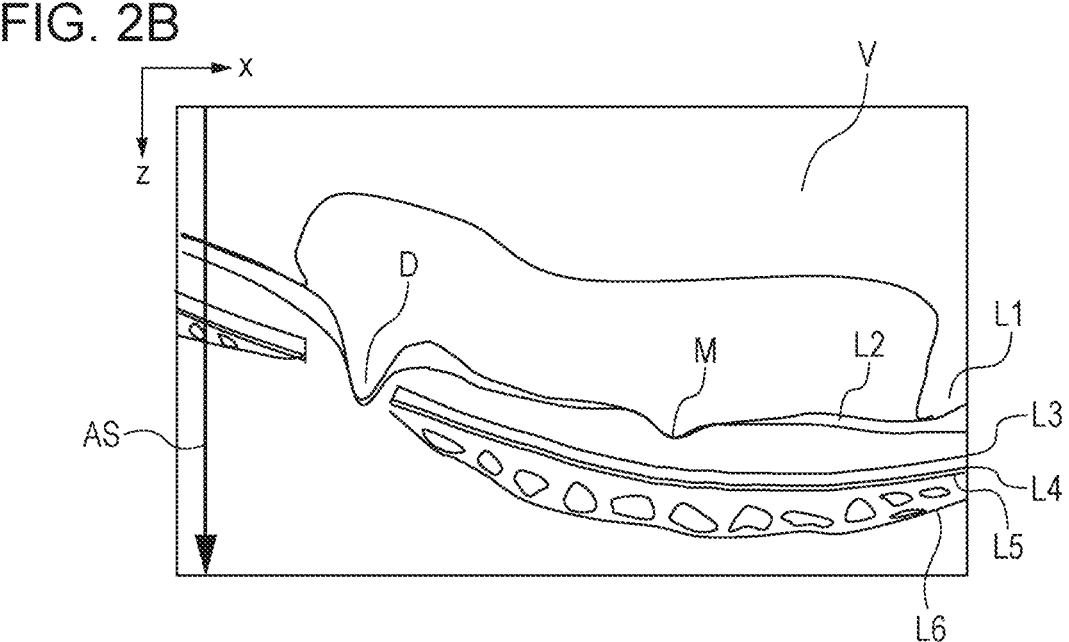
FIG. 2B is a diagram for explaining an example of a tomographic image.
Figure 2C:
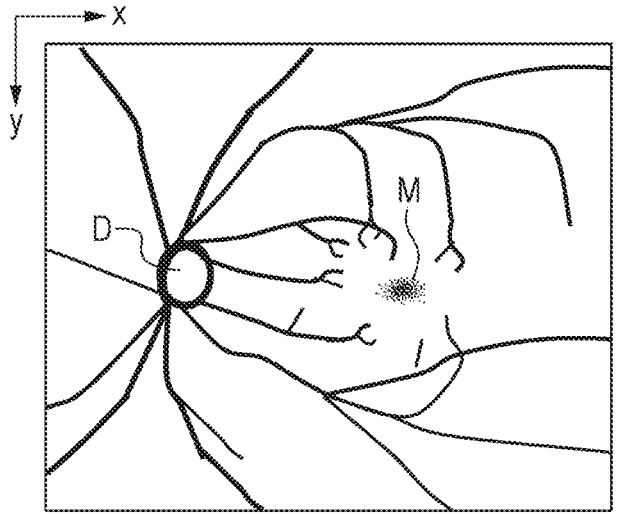
FIG. 2C is a diagram for explaining an example of a fundus image.

In order to accommodate the differences in the axial length, etc. of the subject eye, a coherence gate stage 205 is controlled by the drive control unit 202. "Coherence gate" means a position where the optical distance of measurement light is equal to the optical distance of reference light in OCT. Moreover, as imaging method control, by controlling the position of coherence gate, it is controlled whether to perform imaging on the retinal layer side or a deeper side that is beyond the retinal layer. With reference to FIGS. 2A, 2B, and 2C, an image acquired by the image processing system, and the structure of an eye, will now be explained.

FIG. 2A is a schematic view of an eyeball. In FIG. 2A, C denotes cornea, CL denotes crystalline lens, V denotes vitreous body, M denotes macular area (the center of macula represents fovea), and D denotes optic disk. In the description of the present embodiment, it is assumed that the tomographic imaging apparatus 200 mainly captures an image of the posterior segment of the retina including the vitreous body, the macular area, and the optic disk. The tomographic imaging apparatus 200 may capture an image of the anterior segment including the cornea and the crystalline lens, though not described.

FIG. 2B illustrates an example of a tomographic image acquired by the tomographic imaging apparatus 200 when the retina is imaged. In FIG. 2B, AS represents A scan, which is the unit of image acquisition in OCT tomographic imaging. Plural A scans make up one B scan. The B scan is called as a tomographic image (or tomogram). In FIG. 2B, V denotes vitreous body, M denotes macular area, and D denotes optic disk. L1 denotes a boundary between internal limiting membrane (ILM) and nerve fiber layer (NFL). L2 denotes a boundary between nerve fiber layer and ganglion cell layer (GCL). L3 denotes photoreceptor cell inner/outer segment junction (ISOS). L4 denotes retinal pigment epithelium layer (RPE). L5 denotes Bruch's membrane (BM). L6 denotes choroid. In a tomographic image, the horizontal axis (the direction of main scan of OCT) represents x axis, and the vertical axis (the direction of depth) represents z axis.

An example of a fundus image acquired by the fundus imaging apparatus 400 is illustrated in FIG. 2C. The fundus imaging apparatus 400 is an apparatus that captures a fundus image of an eye. For example, the fundus imaging apparatus 400 is a fundus camera, SLO (Scanning Laser Ophthalmoscope), etc. In FIG. 2C, M denotes macular area, D denotes optic disk, and a thick curve represents a retinal blood vessel. In a fundus image, the horizontal axis (the direction of main scan of OCT) represents x axis, and the vertical axis (the direction of sub scan of OCT) represents y axis. The tomographic imaging apparatus 200 and the fundus imaging apparatus 400 may be integrated into a single device, or may be separated from each other.

The image processing apparatus 300 includes an image acquisition unit 301, a storage unit 302, an image processing unit 303, an instruction unit 304, and a display control unit 305. The image processing apparatus 300 includes, for example, non-illustrated at least one processor and at least one memory. Said at least one processor functions as the image acquisition unit 301, the image processing unit 303, the instruction unit 304, and the display control unit 305 by running a program stored in said at least one memory. The processor is hardware such as, for example, a central processing unit (CPU) or graphics processing unit (GPU). The image acquisition unit 301 includes a tomographic image generation unit 311 and a motion contrast data generation unit 312. The image acquisition unit 301 acquires signal data of a tomographic image captured by the tomographic imaging apparatus 200, and performs signal processing for tomographic image generation and motion contrast data generation. For example, the image acquisition unit 301 acquires a plurality of 2D tomographic images obtained on the basis of measurement light controlled to scan the same position of the eye. The image acquisition unit 301 is an example of an acquisition unit configured to acquire pieces of three-dimensional data of a subject eye (three-dimensional tomographic data of luminance) obtained at different times. The pieces of three-dimensional data may be either data obtained using a scan method based on the same direction of main scan or data obtained using a scan method based on different directions of main scan. The image acquisition unit 301 further acquires fundus image data captured by the fundus imaging apparatus 400. The generated tomographic image and the fundus image are stored into the storage unit 302. The image processing unit 303 includes a preprocessing unit 331, an image generation unit 332, a detection unit 333, a first alignment unit 334, a selection unit 335, a second alignment unit 336, a third alignment unit 337, a fourth alignment unit 338, and an image synthesis unit 339.

The preprocessing unit 331 performs processing for removing artifacts from motion contrast data. The image generation unit 332 generates a 2D motion contrast frontal image (referred to also as OCTA image or En-face image) from 3D motion contrast data (an example of three-dimensional data). The image generation unit 332 is an example of an acquisition unit configured to acquire pieces of three-dimensional data of a subject eye obtained at different times, the three-dimensional data including pieces of two-dimensional data obtained at different positions. The detection unit 333 detects a boundary for each layer from the retina. The first alignment unit 334 performs processing for alignment of 2D frontal images (frontal fundus image). The selection unit 335 selects data taken as a reference from the processing result of the first alignment unit 334. The second alignment unit 336 performs processing for alignment in the horizontal direction (x axis) of the retina using OCTA images. The third alignment unit 337 performs processing for alignment in the depth direction (z axis) of the retina. The fourth alignment unit 338 sets a plurality of areas for alignment at characteristic portion inside a tomographic image, and performs processing for alignment in the depth direction (z axis) of the retina for each area. The image synthesis unit 339 performs processing for summing up and averaging the 3D data aligned by the first to fourth alignment units.

The external storage unit 500 stores information regarding the subject eye (name, age, and gender, etc. of the patient), captured image data, imaging parameters, image analysis parameters, and setting parameters set by an operator, in association with one another.

The input unit 700 includes, for example, a mouse, a keyboard, and a touch operation screen, etc. An operator operates the input unit 700 to give instructions to the image processing apparatus 300, the tomographic imaging apparatus 200, and the fundus imaging apparatus 400.

Figure 3A:
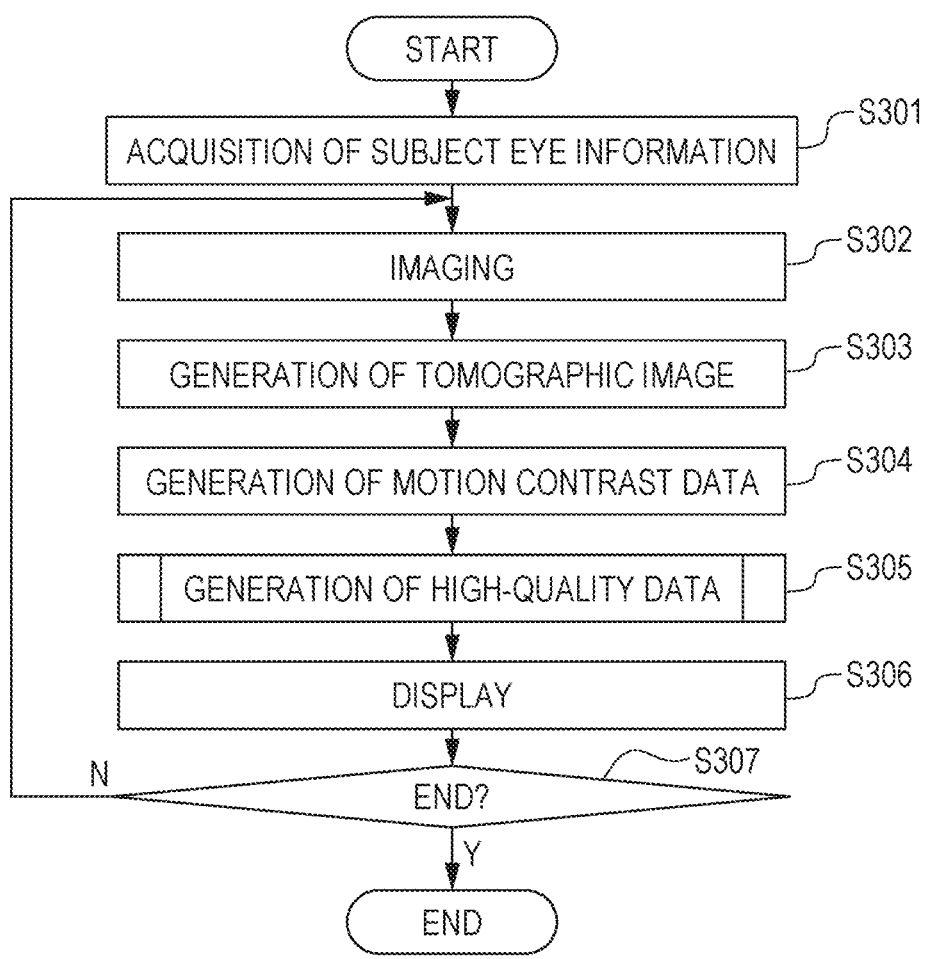
FIG. 3A is a flowchart that illustrates an example of the flow of processing in the image processing system.
Figure 3B:
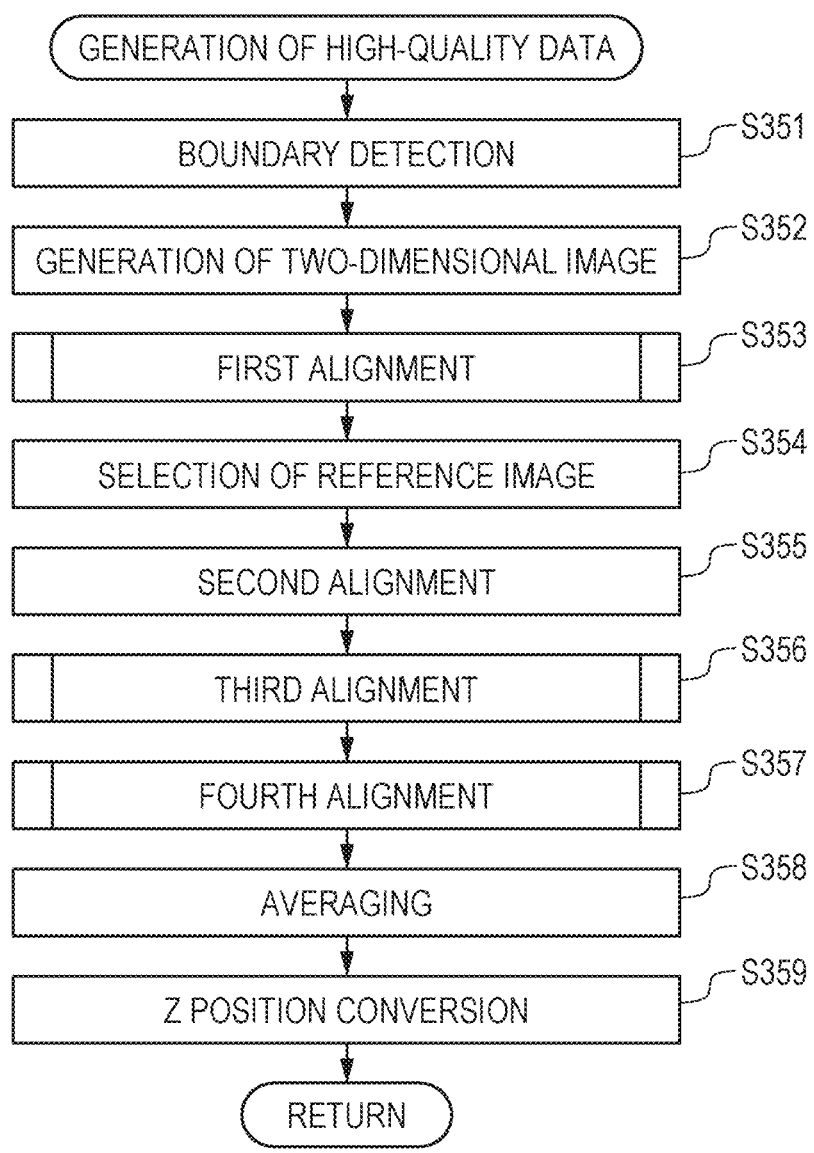
FIG. 3B is a flowchart that illustrates an example of the flow of high-quality data generation processing.
Figure 5:
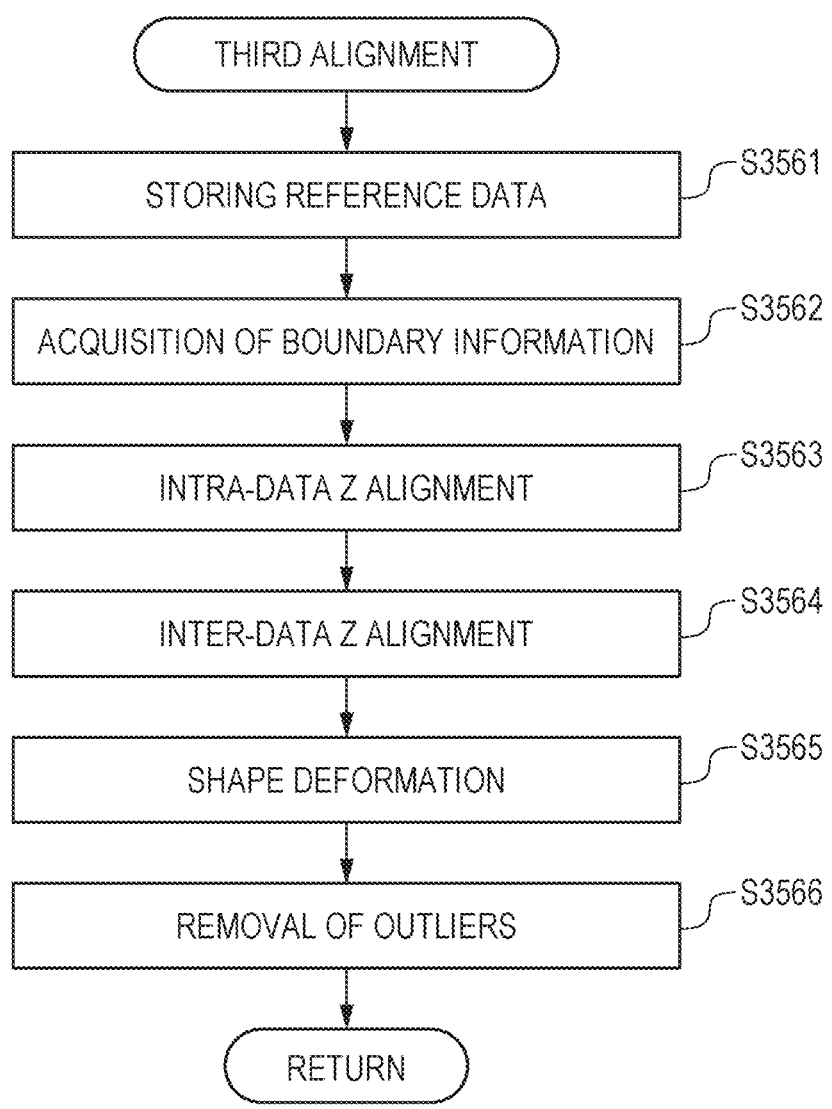
FIG. 5 is a flowchart that illustrates an example of the flow of third alignment processing.
Figure 6:
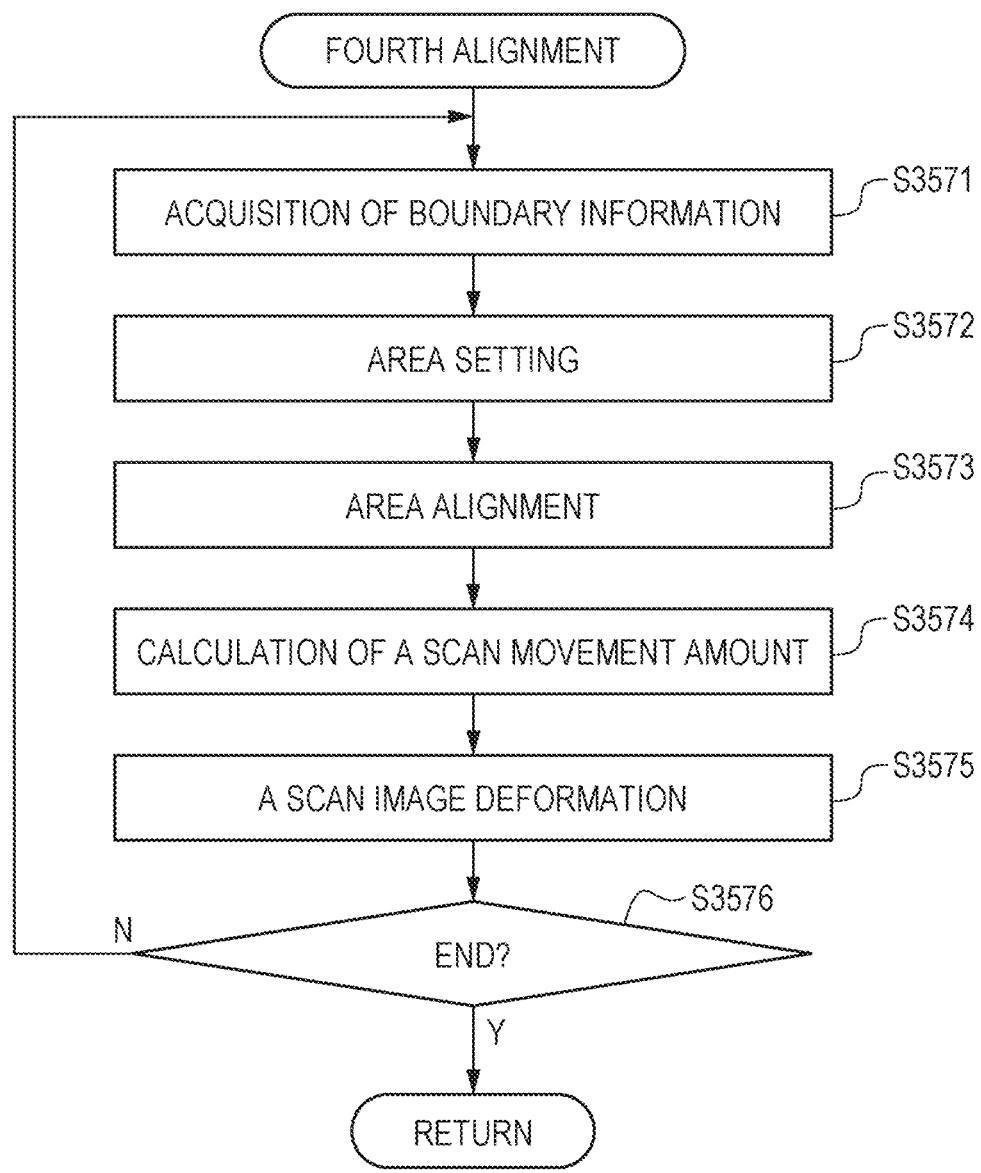
FIG. 6 is a flowchart that illustrates an example of the flow of fourth alignment processing.

Next, with reference to FIGS. 3A and 3B, processing steps of the image processing apparatus 300 of the present embodiment will now be explained. FIG. 3A is a flowchart that illustrates overall operation processing of the system according to the present embodiment. FIG. 3B is a flowchart that illustrates the flow of high-quality image generation processing according to the present embodiment <Step S301>

In S301, a non-illustrated subject eye information acquisition unit acquires a subject person identification number externally as information for identification of the subject eye. Then, on the basis of the subject person identification number, the subject eye information acquisition unit acquires the stored information regarding the subject eye from the external storage unit 500 and stores it into the storage unit 302.

<Step S302>

In S302, the subject eye is scanned and imaged. Subject eye scanning is performed as follows. An operator selects non-illustrated "Start Scan". In response to this start instruction, the tomographic imaging apparatus 200 controls the drive control unit 202 and operates the galvanometer mirror 201 for tomographic image scanning. The galvanometer mirror 201 includes an X scanner for the horizontal direction and a Y scanner for the vertical direction. Therefore, scanning in each of the horizontal direction (X) and the vertical direction (Y) in the apparatus's coordinate system is realized by changing the corresponding direction of these scanners. Therefore, it is possible to perform scanning in a combined direction, which is a combination of the horizontal direction and the vertical direction, by changing the directions of these scanners at the same time. Accordingly, it is possible to perform scanning in an arbitrary direction on the fundus plane.

Before imaging, various imaging parameters are adjusted. Specifically, at least, internal fixation lamp position, scan range, scan pattern, coherence gate position, and focus are set. The drive control unit 202 controls the light emitting diodes of the display unit 241 and controls the position of the internal fixation lamp 204 so as to image the center of the macular area or the optic disk. A scan pattern for 3D volume imaging, for example, raster scan, radial scan, or cross scan, etc. is set. After finishing the adjustment of these imaging parameters, the operator selects non-illustrated "Start Scan" to instruct for imaging.

In the present embodiment, the scan pattern is raster scan for 3D volume imaging, wherein 3D volume is imaged N times (N is 2 or greater) for the purpose of generating high-quality data. The data of N-times-repeated imaging is captured by imaging the same imaging range using the same scan pattern. For example, a range of 3 mm×3 mm is imaged repeatedly by 300×300 (main scan×sub scan). In the 3D volume, the same line position is imaged M times (M is 2 or greater) repeatedly for motion contrast calculation. Specifically, if M is twice, data of 300×600 is actually imaged, and 3D motion contrast data of 300×300 is generated from it. In this specification, the term "the same" is a concept that includes both a case of perfectly the same and a case of approximately the same. For example, a location that is approximately the same, not perfectly the same, could be actually imaged as a result of imperfect tracking or other reason, although it was attempted to image the same location. Such imperfect sameness is also encompassed in the concept of imaging the same position.

In the present embodiment, although detailed description is omitted, the tomographic imaging apparatus 200 scans the subject eye while reducing the effect of involuntary eye movements during fixation by tracking the subject eye so as to image the same location for averaging. Moreover, scanning is performed again automatically at the location of artifact occurrence in a case where motion such as blinking that gives rise to artifacts is detected in the process of image generation.

<Step S303>

In S303, a tomographic image is generated. The tomographic image generation unit 311 performs general and ordinary reconstruction processing on each interference signal to generate a tomographic image.

First, the tomographic image generation unit 311 removes fixed pattern noise from the interference signal. The fixed pattern noise removal is performed by extracting fixed pattern noise by averaging a plurality of A scan signals detected, and then by subtracting the extraction result from the interference signal inputted. Next, the tomographic image generation unit 311 performs predetermined window function processing in order to optimize depth resolution and dynamic range, between which a trade-off relationship holds when Fourier transform is performed in a finite interval. Next, the tomographic image generation unit 311 performs FFT processing to generate a tomographic image.

<Step S304>

Figure 7:
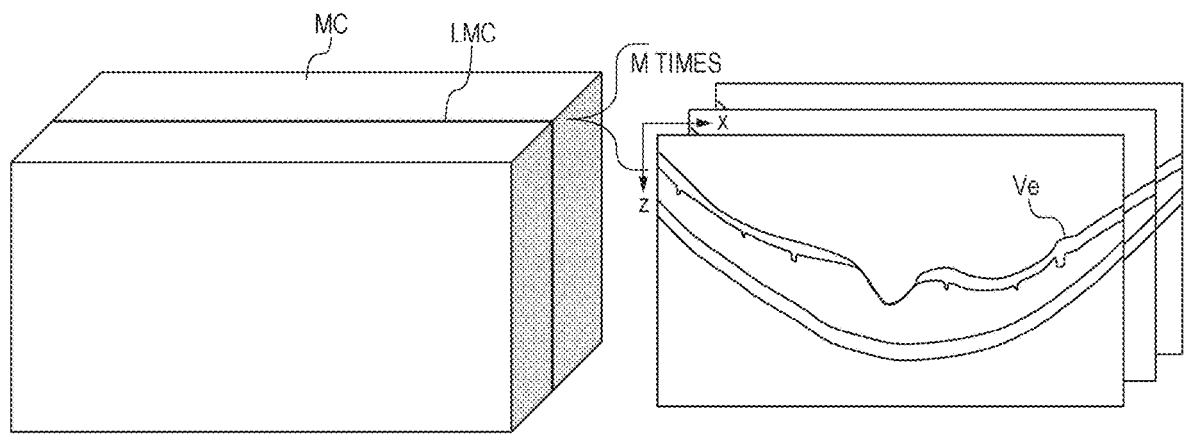
FIG. 7 is a diagram for explaining an example of motion contrast data generation.

In S304, the motion contrast data generation unit 312 generates motion contrast data. With reference to FIG. 7, the generation of this data will now be explained. In FIG. 7, MC denotes 3D motion contrast data, and LMC denotes 2D motion contrast data constituting the 3D motion contrast data. The method of generating LMC will now be explained.

First, the motion contrast data generation unit 312 corrects a position shift, that is, misalignment, between tomographic images captured for the same range of the subject eye. Any method may be used for correcting the misalignment. For example, the motion contrast data generation unit 312 images the same range M times, and aligns pieces of tomographic image data corresponding to the same location with each other by utilizing features such as fundus shape, etc. Specifically, the motion contrast data generation unit 312 selects one of M pieces of tomographic image data as a template, calculates the degree of similarity to other tomographic image data while changing the position and angle of the template, and calculates the amount of position shift from the template. After this processing, the motion contrast data generation unit 312 corrects each piece of tomographic image data on the basis of the calculated amount of position shift.

Next, the motion contrast data generation unit 312 uses Formula 1 to calculate a decorrelation value M (x, z) between two pieces of tomographic image data that are successive in relation to each other in term of imaging time regarding each tomographic image data.

$$M(x, z) = 1 - 2 \times \frac{A(x, z) \times B(x, z)}{A(x, z)^2 + B(x, z)^2} \quad (1)$$

In the above formula, A (x, z) represents luminance at the position (x, z) of tomographic image data A, and B (x, z) represents luminance at the position (x, z), that is, the same position, of tomographic image data B.

The decorrelation value M (x, z) is a value within a range from 0 to 1. The greater the difference between the luminance values of the two, the greater the value of M (x, z). In a case where the number of times M of repetitive acquisition at the same position is three or more, the motion contrast data generation unit 312 is able to calculate a plurality of decorrelation values M (x, z) at the same position (x, z). The motion contrast data generation unit 312 is able to generate final motion contrast data by performing statistical processing such as maximum value calculation or average calculation, etc. on the plurality of decorrelation values M (x, z) calculated. If the number of times M of repetition is 2 (twice), the decorrelation value M (x, z) between the two adjacent pieces of tomographic image data A and B is taken as the value of motion contrast at the position (x, z), instead of performing statistical processing such as maximum value calculation or average calculation, etc.

The mathematical expression for calculating motion contrast shown above, Formula 1, is susceptible to the effect of noise. For example, if noise exists in the non-signal portion of pieces of tomographic image data and if values are different from each other, decorrelation is high, and a motion contrast image will also be contaminated with noise. To prevent this from occurring, the motion contrast data generation unit 312 may perform preprocessing of deeming tomographic data that is less than a predetermined threshold as noise and replacing such a "less-than-threshold" value with zero. This enables the image generation unit 332 to generate a motion contrast image that is less affected by noise on the basis of the generated motion contrast data.

In S305, the image processing unit 303 generates high-quality data. With reference to the flowcharts of FIGS. 3B and 4 to 6 in conjunction with FIGS. 8A and 8B to FIGS. 15A and 15B, processing performed by the image processing unit 303 will now be explained.

<Step S351>

In S351, the detection unit 333 performs retinal layer boundary detection in a plurality of tomographic images captured by the tomographic imaging apparatus 200. The detection unit 333 detects each boundary L1-L6 in the tomographic image illustrated in FIG. 2B or non-illustrated GCL/IPL, IPL/INL, INL/OPL, OPL/ONL. The detection unit 333 applies Median filter and Sobel filter to a tomographic image that is the target of processing, thereby generating filter-applied images respectively (hereinafter referred to as Median image and Sobel image). Next, the detection unit 333 generates profile for each A scan from the generated Median image and the generated Sobel image. The profile is luminance profile for the Median image and gradient profile for the Sobel image. Then, the detection unit 333 detects a peak in the profile generated from the Sobel image. By referring to the Median profile before/after the detected peak and between peaks, the detection unit 333 detects each retinal boundary.

<Step S352>

In S352, the image generation unit 332 generates an OCTA image (En-face image) by projecting, onto a 2D plane, motion contrast data corresponding to a generation range between upper and lower limits specified for 3D motion contrast data. Specifically, the image generation unit 332 generates an OCTA image that is the frontal (en-face) image of a motion contrast image by performing processing such as average intensity projection (AIP) or maximum intensity projection (MIP) on motion contrast data corresponding to a generation range between upper and lower limits among the entire motion contrast data. The method used for generating the OCTA image is not limited to AIP (average value) or MIP (maximum value). Other value such as a minimum value, a median value, a variance value, a standard deviation, or a total sum, etc. may be used instead.

In the present embodiment, for example, the upper limit of the generation range is specified as the ILM/NFL boundary, and the lower limit of the generation range is specified at 50 μm under GCL/IPL in the depth direction. In addition, in the present embodiment, AIP is used for generating the OCTA image. The upper and lower limits of the range for OCTA image generation are not limited to the above example.

Motion contrast data may be generated by the motion contrast data generation unit 312 using tomographic data within the generation range between the upper and lower limits. In such a case, the image generation unit 332 generates an OCTA image on the basis of the generated motion contrast data. By this means, it is possible to generate an OCT image based on tomographic data within the specified range of depth.

<Step S353>

In S353, for N pieces of OCTA images, alignment in the horizontal direction (x axis) and the vertical direction (y axis) of the image and rotational alignment on the x-y plane are performed respectively. This processing will now be explained with reference to the flowchart of FIG. 4.

<Step S3531>

In S3531, the preprocessing unit 331 detects an artifact such as a black band or a white line and removes it from the OCTA image generated by the image generation unit 332. This processing will now be explained with reference to FIGS. 8A and 8B. A black region of an OCTA image illustrated therein represents a region where decorrelation is high, that is, a region where the flow of blood is detected (corresponding to a blood vessel), and a white region of the OCTA image represents a region where decorrelation is low. An example of a black band BB is illustrated in FIG. 8A. An example of a white line WL is illustrated in FIG. 8B. A black band appears due to low decorrelation with a decrease in luminance of a retinal tomographic image when the position of the retina goes away from a high-sensitivity position because of movement during imaging or due to low decorrelation caused by the darkening of the entire image by blinking, etc. A white line appears due to high decorrelation of an image as a whole in a case where alignment of M pieces of tomographic images for decorrelation calculation is poor or in a case of failure to correct the position by alignment. Since these artifacts appear in decorrelation calculation, the unit of artifact occurrence is one line in the direction of main scan. Therefore, the preprocessing unit 331 performs artifact detection on a line-by-line basis.

For example, in black band detection, the detection result is "black band" in a case where the average value of decorrelation on one line is not greater than a threshold $TH_{AVG\_B}$. In white line detection, the detection result is "white line" in a case where the average value of decorrelation on one line is not less than a threshold $TH_{AVG\_W}$ and in addition where the standard deviation (or variance value) is not greater than a threshold $TH_{SD\_W}$. If determination for white line detection is performed solely on the basis of the average value, since decorrelation could be high for a major blood vessel, etc., there is a possibility that a region containing a blood vessel with such high decorrelation will be erroneously detected as a white line. To avoid such a detection error, determination is performed on the basis of a combination of the threshold and an index for evaluating variation in values such as a standard deviation or a variance value. Specifically, one line that includes a blood vessel with high decorrelation has a large average value and a large standard deviation. By contrast, one line of white line has a small standard deviation because of less variation, although its average value is large. The value of decorrelation of an OCTA image varies depending on whether the eye is healthy or affected with a disease and depending on, for the affected eye, the type of the disease. Therefore, it is more advantageous to set the threshold on an image-by-image basis in accordance with the brightness of an OCTA image by using a dynamic threshold method such as P-tile or determination analysis. In a case where a dynamic threshold method is employed, an upper-limit threshold and a lower-limit threshold have been set in advance, and the upper-limit threshold or the lower-limit threshold is set as the threshold if above or below the preset value.

The preprocessing unit 331 stores each area of artifact found as described above into a Mask image corresponding to the OCTA image. In the Mask image illustrated in FIGS. 8A and 8B, an example of setting "1" for a white area and setting "0" for a black area is shown.

<Step S3532>

In S3532, the first alignment unit 334 initializes a two-dimensional matrix used for storing alignment parameters when each OCTA image is aligned. Information that is necessary for ensuring high image quality such as parameters of deformation during alignment and the degree of image similarity are stored together into matrix elements.

<Step S3533>

Figure 9A:
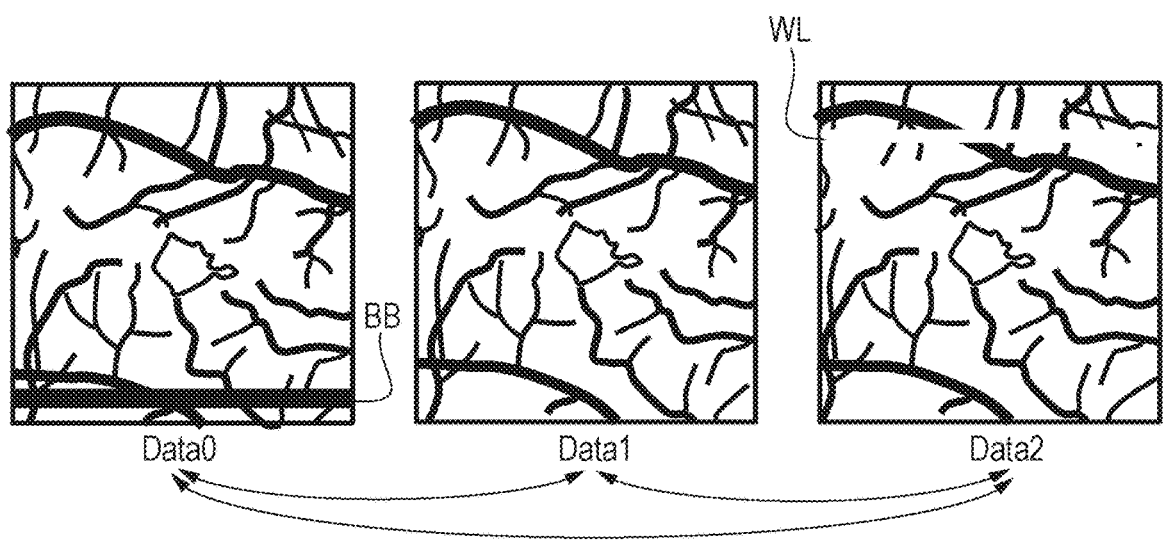
FIG. 9A is a diagram for explaining an example of first alignment.
Figure 9B:
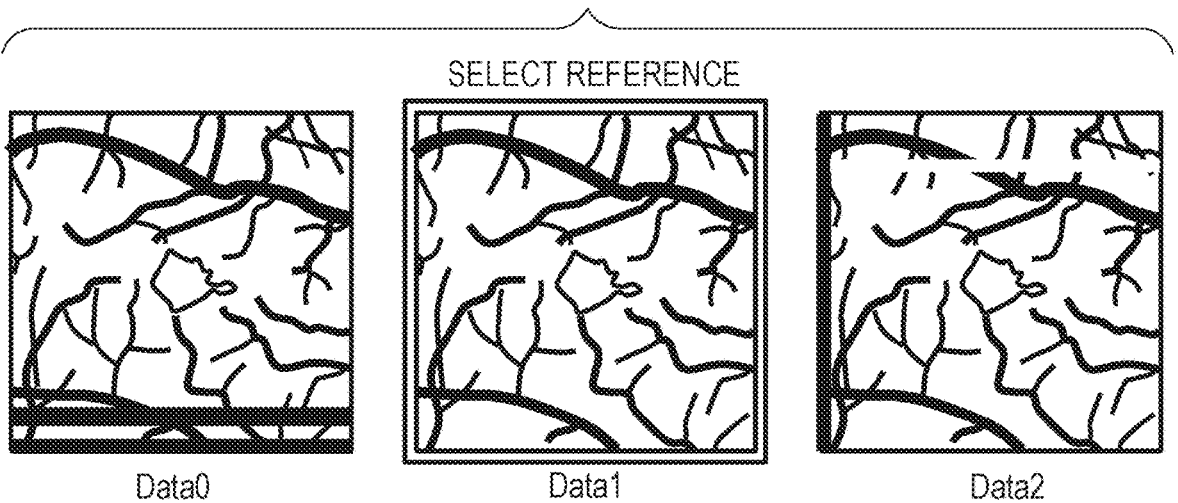
FIG. 9B is a diagram for explaining an example of first alignment.

In S3533, the first alignment unit 334 selects the target of alignment. In the present embodiment, every OCTA image is to be set as a reference image for alignment with the other OCTA images. Therefore, in S3533, in a case where the OCTA image of Data 0 is taken as a reference, alignment with each of Data 1 to Data (N−1) is performed. Next, in a case where the OCTA image of Data 1 is taken as a reference, alignment with each of Data 2 to Data (N−1) is performed. Next, in a case where the OCTA image of Data 2 is taken as a reference, alignment with each of Data 3 to Data (N−1) is performed. The processing is repeated in this way. An example of the processing is illustrated in FIG. 9A. For simplicity, Data 0 to Data 2 only are illustrated in FIGS. 9A and 9B. However, alignment is performed between N pieces of OCTA images if 3D volume is imaged N times.

As disclosed herein, when Data of the reference image is incremented by one, Data of the target image from which alignment is started is also incremented by one. This will now be explained using an example of a case where the OCTA image of Data 2 is taken as a reference. When the OCTA image of Data 2 is taken as a reference, alignment of Data 0 with Data 1, alignment of Data 0 with Data 2, and alignment of Data 1 with Data 2 have already been done as the result of processing done before it. Therefore, when the OCTA image of Data 2 is taken as a reference, beginning with alignment with Data 3 suffices. For this reason, despite the fact that all OCTA images are to be aligned with one another, calculation for one half of all combinations suffices.

<Step S3534>

In S3534, the first alignment unit 334 performs alignment in the horizontal direction (x axis) and the vertical direction (y axis) of the image and rotational alignment on the x-y plane between the plurality of OCTA images. That is, the first alignment unit 334 is an example of a first planar alignment unit configured to perform alignment in a plane orthogonal to a depth direction.

In alignment between OCTA images, in order to perform sub-pixel alignment on the x-y plane, OCTA image size is increased. Higher alignment precision can be expected by performing sub-pixel alignment as compared with pixel alignment. For example, if OCTA imaging size is 300×300, it is enlarged to 600×600. An interpolation method such as Bicubic interpolation or Lanczos (n) interpolation is used for enlargement. For example, the following processing is performed for aligning one image with another. An evaluation function that expresses the degree of similarity of two OCTA images to each other has been defined in advance. An evaluation value is calculated while shifting and rotating the OCTA image position. The location where the best evaluation score is obtained is adopted as the alignment result. Regarding the evaluation function, a method of evaluation based on pixel values can be used (for example, a correlation coefficient is used for evaluation).

Formula 2 for a case of using a correlation coefficient as the evaluation function expressing the degree of similarity is shown below.

$$\frac{\int\int_s (f(x,y)-\overline{f})(g(x,y)-\overline{g})dxdy}{\sqrt{\int\int_s (f(x,y)-\overline{f})^2 dxdy \int\int_s (g(x,y)-\overline{g})^2 dxdy}} \qquad (2)$$

In Formula 2, the area of the OCTA image of Data 0 is defined as f (x, y), and the area of the OCTA image of Data 1 is defined as g (x, y).

$$\overline{f},\overline{g} \qquad (3)$$

Formula 3 shown above expresses the average of the area f (x, y) and the area g (x, y) respectively. The area mentioned here is an image region used for alignment. An area smaller than OCTA image size is usually set, and ROI size shown above is set.

The evaluation function is not limited to the above example, and SSD (Sum of Squared Difference) or SAD (Sum of Absolute Difference) may be used instead; it is sufficient as long as it is possible to evaluate the degree of similarity between images or the degree of difference between images. Alternatively, POC (Phase Only Correlation) may be used for alignment. Non-local "big picture" alignment on the x-y plane is performed through this processing.

Although an example of performing alignment involving an increase in OCTA image size is described above, the scope of the disclosure is not limited to this example. Enlargement is not always necessary. If the input OCTA image size is based on high-density scanning, for example, 900×900, enlargement may be skipped. In order to perform alignment at a high speed, pyramid structure data may be generated.

<Step S3535>

In S3535, the first alignment unit 334 calculates the image evaluation value of the OCTA images. The image evaluation value is calculated using the common image area not including any invalid area arising from alignment between the OCTA images that have already been 2D-aligned in S3534. For example, it is possible to calculate the image evaluation value Q using Formula 4.

$$Q = \frac{\sigma_{fg}}{\sigma_f \sigma_g} \cdot \frac{2\overline{f}\overline{g}}{(\overline{f})^2+(\overline{g})^2} \cdot \frac{2\sigma_f \sigma_g}{\sigma_f^2+\sigma_g^2} \qquad (4)$$

In the formula, the area of the OCTA image of Data 0 is defined as f (x, y), and the area of the OCTA image of Data 1 is defined as g (x, y). The first term represents a correlation coefficient similarly to Formula 2. Therefore, $\sigma_f$ and $\sigma_g$ in the formula correspond to those shown in Formula 2 respectively. The second term is a term for evaluating brightness level.

$$\overline{f},\overline{g} \qquad (5)$$

Formula 5 shown above expresses the average of the area f (x, y) and the area g (x, y) respectively. The third term is a term for evaluating contrast. The minimum value of each term is 0, and the maximum value of each term is 1. For example, the evaluation value is 1 if Data 0 is the same as Data 1. Therefore, a high evaluation score will be obtained in a case where average one among the N pieces of OCTA images is taken as a reference. The evaluation score will be low in a case where an OCTA image that is different from the other OCTA images is taken as a reference. The phrase "different from the other OCTA images" applies to the following cases: its imaging position is different therefrom; the image is distorted; the image as a whole is too dark or too bright; the image contains an artifact such as a white line or a black band. It is not always necessary that the image evaluation be based on the above formula. Each term may be evaluated individually. The combination may be modified.

<Step S3536>

In S3536, the first alignment unit 334 stores values into the two-dimensional matrix initialized in S3532 for storing parameters necessary for ensuring high image quality such as parameters regarding alignment and the degree of image similarity. For example, if Data 0 is taken for the reference image and Data 1 is taken for the target image, horizontal alignment parameter X, vertical alignment parameter Y, X-Y-plane rotational parameter a, image evaluation value, and the degree of image similarity are stored into the element (0, 1) of the two-dimensional matrix. In addition to these items of information, the Mask image illustrated in FIGS. 8A and 8B is stored in association with the OCTA image. Magnification may be stored if magnification correction is performed, though not described in the present embodiment.

<Step S3537>

In S3537, the first alignment unit 334 determines whether or not all of the images have already been set as the reference image for alignment with the other images. The process returns to S3533 if not all of the images have been set as the reference image. The process proceeds to S3538 if all of the images have already been set as the reference image.

<Step S3538>

In S3538, the first alignment unit 334 updates the remaining elements of the two-dimensional matrix. As explained in S3533, the above calculation has been done only for one half of all combinations. Therefore, these values are copied into the corresponding "not-calculated" element. For example, the parameters in the element (0, 1) of the two-dimensional matrix are copied into the element (1, 0). That is, copying from the element (i, j) to the element (j, i) is performed. Since the alignment parameters X and Y and the rotational parameter a should be inverted, the values of them are copied after minus-sign multiplication. Since the degree of image similarity, etc. should not be inverted, the same value is copied as it is. OCTA image alignment is performed through these processing steps. Referring back to the processing flow in FIG. 3B, the next step will now be explained.

<Step S354>

In S354, the selection unit 335 selects a reference image. The selection of a reference image is performed on the basis of the result of alignment done in S353. In S353, a two-dimensional matrix was generated, and information necessary for generating an image with high quality was stored into each element of the matrix. Therefore, a reference image is selected using the stored information. An image evaluation value, an alignment parameter evaluation value, and an artifact area evaluation value are used in the selection of a reference image. As the image evaluation value, the value that was calculated in S3535 is used. The alignment parameter evaluation value SV is calculated by, for example, Formula 6 using the alignment results X and Y that were found in S3534. In Formula 6, the larger the amount of movement, the greater the value.

$$SV = \sqrt{X^2 + Y^2} \qquad (6)$$

The artifact area evaluation value is calculated by, for example, Formula 7 using the Mask image that was found in S3531. In Formula 7, T (x, y) represents pixels in a non-artifact area in the Mask image. A (x, y) represents all pixels in the Mask image. Therefore, the maximum value is 1 in a case where no artifact exists.

$$NA = \frac{\sum_{(x,y)}^{n} T_{(x,y)}}{\sum_{(x,y)}^{n} A_{(x,y)}} \qquad (7)$$

The greater the image evaluation value, the better. The greater the artifact area evaluation value, the better. The less the alignment parameter evaluation value, the better. Since the image evaluation value and the alignment parameter evaluation value are values determined in relation to the other images when a certain image is taken as the reference, they are the sum of N−1 pieces. Since the criteria of evaluation for these evaluation values are different from one another, sorting is performed for each of these values, and a reference image is selected on the basis of the sum of sorted index values. For example, sorting is performed such that the following relation holds. The greater the image evaluation value, the smaller the after-sorting index. The greater the artifact area evaluation value, the smaller the after-sorting index. The less the alignment parameter evaluation value, the smaller the after-sorting index. An image that minimizes the after-sorting index is selected as the reference image.

Although an example of selecting a reference image by performing sort value summation is described above, the method of selecting a reference image is not limited to this example. The evaluation value may be calculated with weighting on the after-sorting index of each of the evaluation values.

Alternatively, instead of using sort values, calculation may be performed with normalization such that each of the evaluation values becomes equal to 1. For example, although the image evaluation value is normalized to 1, since it is the sum of N−1 pieces in the present embodiment, an average value can be used.

It is possible to normalize the alignment parameter evaluation value to one if defined as expressed in Formula 8 below. In this case, the closer the evaluation value to 1, the better the evaluation value.

$$NSV_n = 1.0 - \alpha \frac{SV_n}{SV_{max}} \qquad (8)$$

In Formula 8, $SV_n$ is the sum of N−1 pieces of the values calculated using Formula 6, and the subscript n corresponds to Data number. Therefore, for Data 0, $SV_0$. $SV_{max}$ is the maximum alignment parameter evaluation value between Data 0 and Data (N−1). Weight a is an adjustment parameter for specifying the setting value of $NSV_n$ when $SV_n$ is the same as $SV_{max}$. The maximum value $SV_{max}$ may be determined from actual data as described above or may have been defined as a threshold in advance.

The artifact area evaluation value may be used as it is, because it has been normalized to 0 to 1.

In a case where all of the evaluation values are normalized to 1 as described above, one that maximizes the sum of the evaluation values is selected as the reference image.

An image that best satisfies the following conditions is selected as the reference image described herein: an image that has average characteristics among the N pieces of images, is relatively small in terms of the amount of movement when aligned with the other images, and is less affected by artifacts. An example of the reference image selected is illustrated in FIG. 9B. In this example, Data 1 is selected as the reference image. Each of Data 0 and Data 2 is moved on the basis of the alignment parameters calculated by the first alignment unit 334.

<Step S355>

Figure 10A:
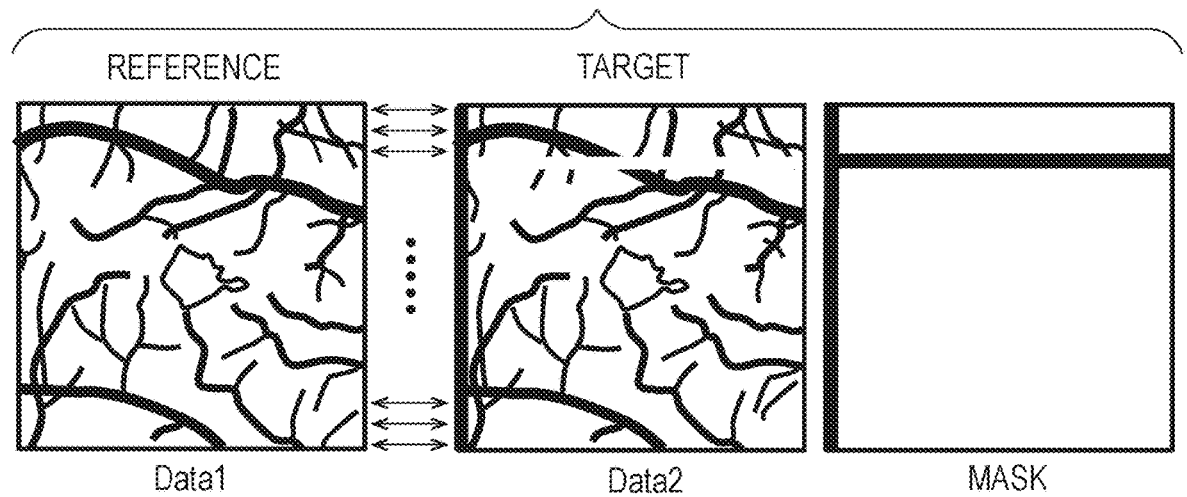
FIG. 10A is a diagram for explaining an example of second alignment.

In S355, the second alignment unit 336 performs processing for alignment in the horizontal direction (x axis) of the retina using OCTA images. This processing will now be explained with reference to FIGS. 10A and 10B. An example of alignment in the horizontal direction for a case where the reference image is Data 1 and the alignment target is Data 2 is shown in FIG. 10A. In the Mask image, zero is set for an artifact included in Data 2 (the horizontal black line in the drawing) and for an invalid area (the vertical black line in the drawing) arising from movement of Data 2 as a result of alignment with Data 1. The reference image and the alignment target image undergo alignment on each line, and the degree of similarity is calculated on a line-by-line basis. For example, Formula 2 is used for calculating the degree of similarity. The line is moved to the position where the degree of similarity is maximized. A weight is set to the Mask in accordance with the degree of similarity to the reference image, calculated on a line-by-line basis.

Figure 10B:
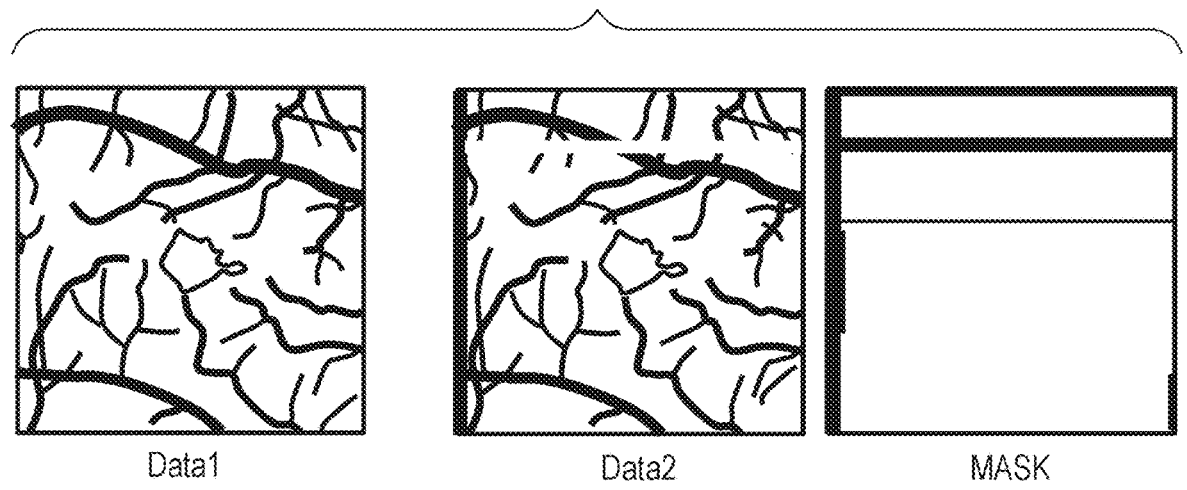
FIG. 10B is a diagram for explaining an example of second alignment.

An example of the result of alignment by the second alignment unit 336 is illustrated in FIG. 10B. The example illustrated in FIG. 10B shows that it is determined that the alignment target image does not resemble the reference image at the upper end portion of the image and near the center of the image, and horizontal black lines are set in the Mask image as lines that are not used for overlaying. The example further shows shifting to the left near the center of the image and shifting to the right at the lower end portion of the image as the result of alignment on a line-by-line basis. Since the shifting of the image gives rise to an invalid area, zero is set in the invalid area of the Mask. Local alignment on the x-y plane is performed through this processing.

The rotational parameter a calculated in the first alignment may be applied to each image before performing the second alignment or may be applied thereto after performing the second alignment.

<Step S356>

In S356, the third alignment unit 337 performs alignment in the depth direction (z direction) for reference 3D data and other 3D data. This processing will now be explained with reference to the flowchart of FIG. 5.

<Step S3561>

In S3561, the third alignment unit 337 stores 3D motion contrast data taken as a reference and 3D tomographic image data taken as a reference. For example, in the present embodiment, 3D motion contrast data and 3D tomographic image data of Data 1 are stored.

<Step S3562>

In S3562, the third alignment unit 337 acquires the boundary information that was detected in S351. In the present embodiment, for example, the boundary used for alignment in the depth direction is L1. However, the scope of the disclosure is not limited to this example.

<Step S3563>

Figure 11A:
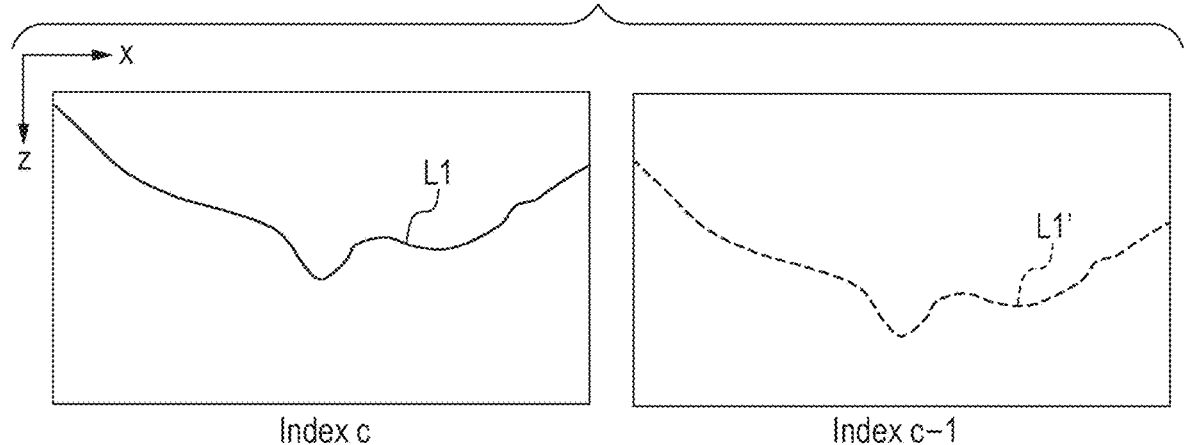
FIG. 11A is a diagram for explaining an example of third alignment.

In S3563, the third alignment unit 337 performs alignment in terms of position in the depth direction, and slope, for each piece of 3D data. The eye is moving when a 3D tomographic image is captured. Regarding movement on the x-y plane, alignment is almost done at the time of imaging because imaging is performed while performing tracking on a real-time basis. However, since real-time tracking is not performed in the depth direction, it is necessary to perform intra-data alignment. That is, the description here relates to alignment inside a single piece of 3D data. This processing will now be explained with reference to FIGS. 11A, 11B, and 11C. An example of a boundary used for alignment is illustrated in FIG. 11A. In the present embodiment, it is assumed that the boundary L1 (ILM) is used. Although a case of using the boundary L1 is explained here, the boundary used is not limited to L1. Any other boundary may be used instead. Alternatively, a plurality of boundaries may be used in combination.

In FIG. 11A, the reference data is depicted as Index c, and the target data is depicted as Index c-1. The initial reference data is taken at the center boundary of the 3D data, and the initial target data is taken at an adjacent boundary that is next to the reference data in the direction of sub scan.

Figure 11B:
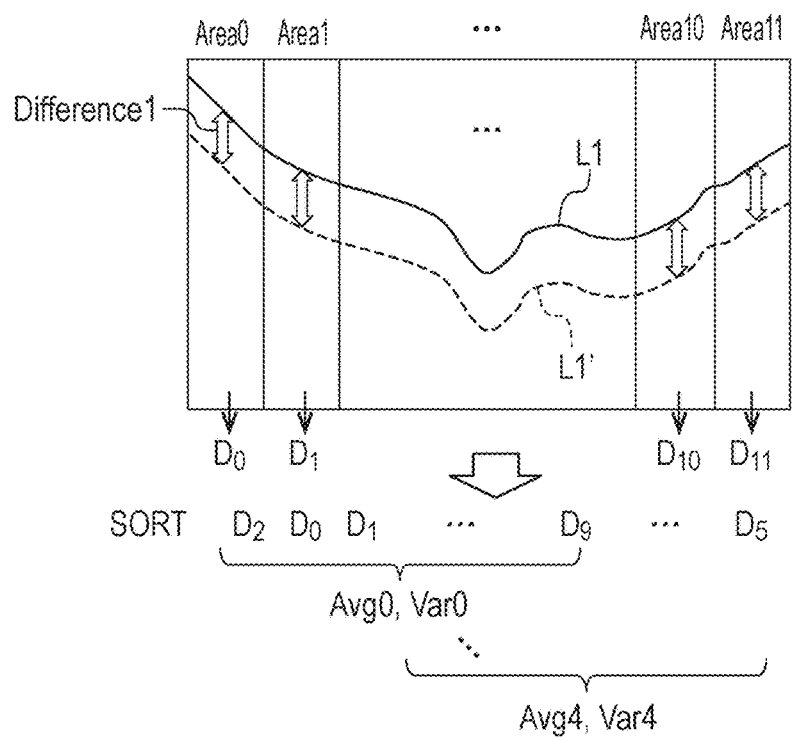
FIG. 11B is a diagram for explaining an example of third alignment.

For the purpose of explanation, the boundary L1 of the reference data and the boundary L1' of the alignment target are shown together in FIG. 11B. In FIG. 11B, the boundary is divided into twelve columnar segments. In the present embodiment, the number of the segments is twelve. These segmental areas are labeled as Area 0 to Area 11. Although no segmental area is shown at the center portion in FIG. 11B, actually, the entire image is divided into these segments. Each vertical double-headed arrow Difference 1 represents the difference between L1 and L1'. The difference indicated by this arrow is calculated in each of Area 0 to Area 11. The number of the segments may be changed in accordance with image size in the horizontal direction. Alternatively, it may be changed in accordance with horizontal boundary width size detected in common. In the present embodiment, for simplicity, horizontal boundary size is shown to be equal. However, actually, a retinal layer could shift upward in the image (the direction toward zero on the z axis), resulting in that a regional part of the retinal layer is missing from the image. In such a case, complete boundary detection throughout the entire image is impossible. Therefore, the boundary-with-boundary alignment should be performed with division of a range in which the boundary L1 of the reference data and the boundary L1' of the alignment target are detectable.

Figure 11C:
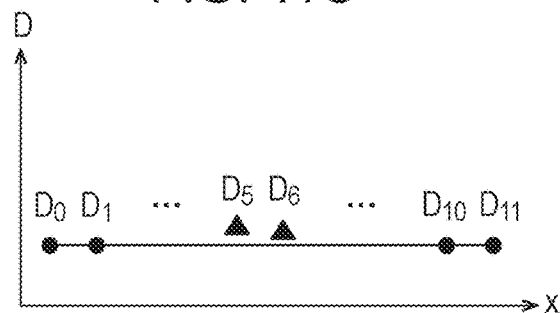
FIG. 11C is a diagram for explaining an example of third alignment.

In FIG. 11B, the average of Difference 1 of each area is defined as $D_0, \ldots, D_{11}$. That is, the average of the difference of ILM is taken as the representative value of the difference of the area each. Next, the representative values Do to Di calculated for the respective areas are sorted in ascending order. Then, average and variance are calculating using, among the sorted representative values, eight values counted in ascending order. Although the number of the values selected is eight in the present embodiment, the number of the values selected is not limited to this example. It is sufficient as long as the number of the values selected (selection) is less than the number of the segments (division). The calculation of average and variance is performed while shifting the sorted representative values one by one. That is, since the calculation is performed using the eight representative values among those of the twelve segmental areas in the present embodiment, five kinds of average and variance are found in total. Next, a shift value in the depth direction, and slope, are calculated using eight representative values of the difference, wherein said eight values are those on the basis of which the minimum variance among the five kinds of variance found has been calculated. This calculation will now be explained with reference to FIG. 11C and Formula 9. FIG. 11C is a graph whose horizontal axis represents the center x coordinates of the segmental areas and whose vertical axis represents the representative values of the difference. In FIG. 11C, black dots represent an example of a combination of representative values of the difference for which the variance value is minimized, and black triangles represent an example of non-selected representative values of the difference. Calculation in Formula 9 below is performed using the combination of representative values of the difference for which the variance value is minimized (shown as black dots in FIG. 11C).

$$D = ax + b \tag{9}$$

$$a = \frac{n\sum_{i=1}^{n} x_i D_i - \sum_{i=1}^{n} x_i \sum_{i=1}^{n} D_i}{n\sum_{i=1}^{n} x_i^2 - \left(\sum_{i=1}^{n} x_i\right)^2} \tag{10}$$

$$b = \frac{\sum_{i=1}^{n} x_i^2 \sum_{i=1}^{n} D_i - \sum_{i=1}^{n} x_i D_i \sum_{i=1}^{n} x_i}{n\sum_{i=1}^{n} x_i^2 - \left(\sum_{i=1}^{n} x_i\right)^2} \tag{11}$$

In Formula 9, D denotes a shift value in the depth direction, and x denotes x coordinate, that is, A scan position. Calculation regarding a and b in Formula 9 is shown in Formula 10 and Formula 11 respectively. In Formula 10 and Formula 11, $x_i$ denotes the center x coordinate of the segmental area for the selected representative value each, Di denotes the selected representative value of the difference each, and n denotes the number of the selected representative values, that is, n=8 in the present embodiment. From Formula 9, a shift value in the depth direction for each A scan is calculated.

As described herein, area segmentation is performed when boundary alignment is performed, and the combination of values that minimize variation among the values of the difference of the segmental areas is used; accordingly, even if there is an error in boundary detection, the values of the areas regarding the error are not used. Therefore, it is possible to calculate a shift value in the depth direction stably. Although average is used as the representative value in the depth direction of each area in the present embodiment, median may be used instead. It is sufficient as long as the value used is representative. Although variance is used as the value of variation in the present embodiment, standard deviation may be used instead. It is sufficient as long as the value used serves as a measure for evaluating variation.

The processing for alignment described above is performed for all pieces of data while changing the reference data and the target data. Specifically, as described earlier, the initial reference data has been taken at the center boundary of the 3D data, and the initial target data has been taken at an adjacent boundary that is next to the reference data. After completion of this alignment, next, the data that was the target in the now-completed processing is taken as the reference data, and the data adjacent thereto is taken as the target data, and alignment is performed. After completion of the processing up to the end of the image, the reference data is taken at the center boundary again, and the target data is taken at the opposite adjacent boundary, which is next to the reference data on the opposite side, and alignment is performed. The processing is performed up to the end of the image on the opposite side, too. If there is any data for which layer detection has not been successfully performed, correction is performed using the preceding alignment parameter, which is immediately before said non-detected one, and the process proceeds to the next data.

Figures 12A, 12B:
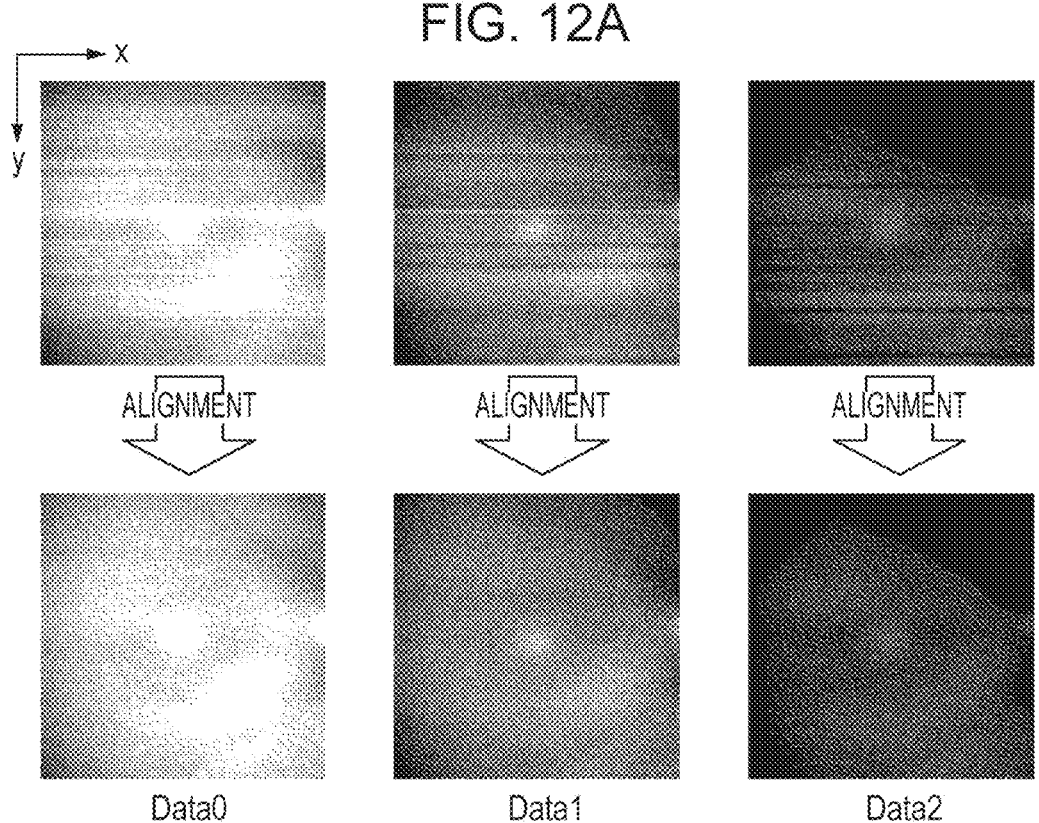
FIG. 12A is a diagram for explaining an example of the result of third alignment.
FIG. 12B is a diagram for explaining an example of the result of third alignment.

An example of application of the processing described above is illustrated in FIG. 12A. FIG. 12 shows Depth Map in which the z coordinates of the boundary L1 are expressed as luminance values. Specifically, bright Depth Map indicates that the z-coordinate values are large, and dark Depth Map indicates that the z-coordinate values are small. Data 0, Data 1, and Data 2 are shown in FIG. 12A. The upper Depth Map corresponds to "before alignment". The lower Depth Map corresponds to "after alignment". Depth Map before alignment contains unevenness in color in the horizontal direction in all of the illustrated pieces of data. This indicates that the retina is moving in the z direction during imaging. By contrast, Depth Map after alignment does not contain unevenness in color in the horizontal direction, showing that the z-directional position is aligned between the adjacent pieces of data. Although an example of performing alignment on the opposite side after performing alignment on one side of data in the depth-directional alignment is described above, the scope of the disclosure is not limited to this example. Processing on both sides may be performed in parallel, with the same initial reference data taken.

The third alignment unit 337 stores the movement amount in the depth direction of each A scan of the reference data (in the present embodiment, Data 1).

Through the processing in the step described above, alignment in the depth direction of a tomogram in the y direction (the direction of sub scan) is performed. That is, the third alignment unit 337 is an example of a first depth alignment unit configured to perform fundus-depth-directional alignment in the direction of sub scan inside three-dimensional data.

<Step S3564>

In S3564, the third alignment unit 337 performs alignment in terms of position in the depth direction, and slope, between the pieces of 3D data. In this step, alignment between the pieces of 3D data is performed using the result of alignment in the depth direction inside the 3D data each in S3563. Similarly to the alignment described above, the boundary L1 is used for the alignment in this step. The method of calculation is the same as that of S3563. However, calculation in this step is not intra-data calculation but inter-data calculation. Therefore, alignment between reference data and target data is performed. This processing will now be explained with reference to FIG. 12B. In the present embodiment, it is assumed that the reference data is Data 1, and the alignment target data is Data 0 and Data 2. Therefore, Depth Map of each of Data 0 and Data 2 is deformed by applying the parameters calculated through the first alignment and the second alignment thereto. Then, for both of Data 0 and Data 2, depth-directional alignment, with Data 1, based on the boundary L1 corresponding to each B scan is performed. The same formula as Formula 9 is used for calculation for them.

Data 0, Data 1, and Data 2 are shown in FIG. 12B. The upper Depth Map corresponds to "after intra-data alignment". The lower Depth Map corresponds to "after inter-data alignment". In Depth Map after intra-data alignment, the brightness of Depth Map differs because of the difference in the z position of the retina between Data 0, Data 1, and Data 2. By contrast, in Depth Map after inter-data alignment, the difference in brightness of Depth Map is reduced because of the reduced difference in the z position of the retina between Data 0, Data 1, and Data 2.

Non-local "big picture" alignment in the z direction is performed through the processing described above.

<Step S3565>

In S3565, the third alignment unit 337 performs 3D data deformation by applying the deformation parameters regarding X, Y, Rotation, and Z obtained through the first alignment, the second alignment, and the third alignment to the 3D data. Both the 3D data tomographic image data and the 3D motion contrast data are deformed. In a case where image enlargement on the x-y plane was performed for alignment in S3534, processing for returning to deformation parameters corresponding to the original size is performed when 3D data deformation is performed. Specifically, in a case where the numerical value of the x-y-plane alignment parameter of a double-size-enlarged image is 1, the value is reduced to 0.5 in this step. Then, the deformation of the 3D data based on the original size is performed.

In a case where the deformation parameters regarding X, Y, Rotation, and Z define the amount of movement in terms of sub pixel or sub voxel when the 3D data is converted, the 3D data is deformed by performing interpolation processing. Data generated by interpolation processing is an example of interpolation data. In a case where interpolation data is generated for each of the pieces of 3D data, it follows that alignment is performed between pieces of interpolation data in the step described below. The term "sub pixel" or "sub voxel" refers to a case where the amount of movement is in a real number such as 0.5, a case where the Rotation parameter is not zero and data is rotated, or the like. For interpolation of the shape data, Bicubic interpolation or Lanczos (n) interpolation, etc. is used.

Figure 13:
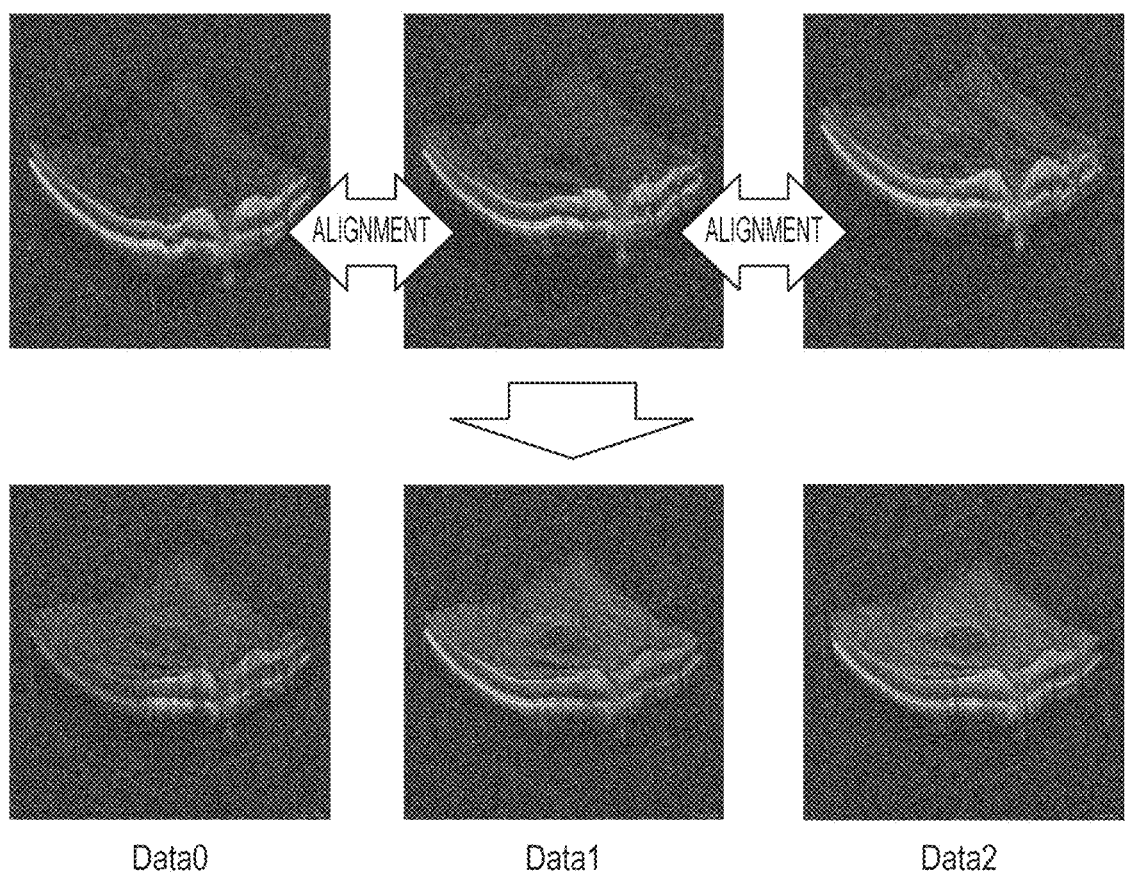
FIG. 13 is a diagram for explaining an example of the result of three-dimensional data deformation.
Figure 14:
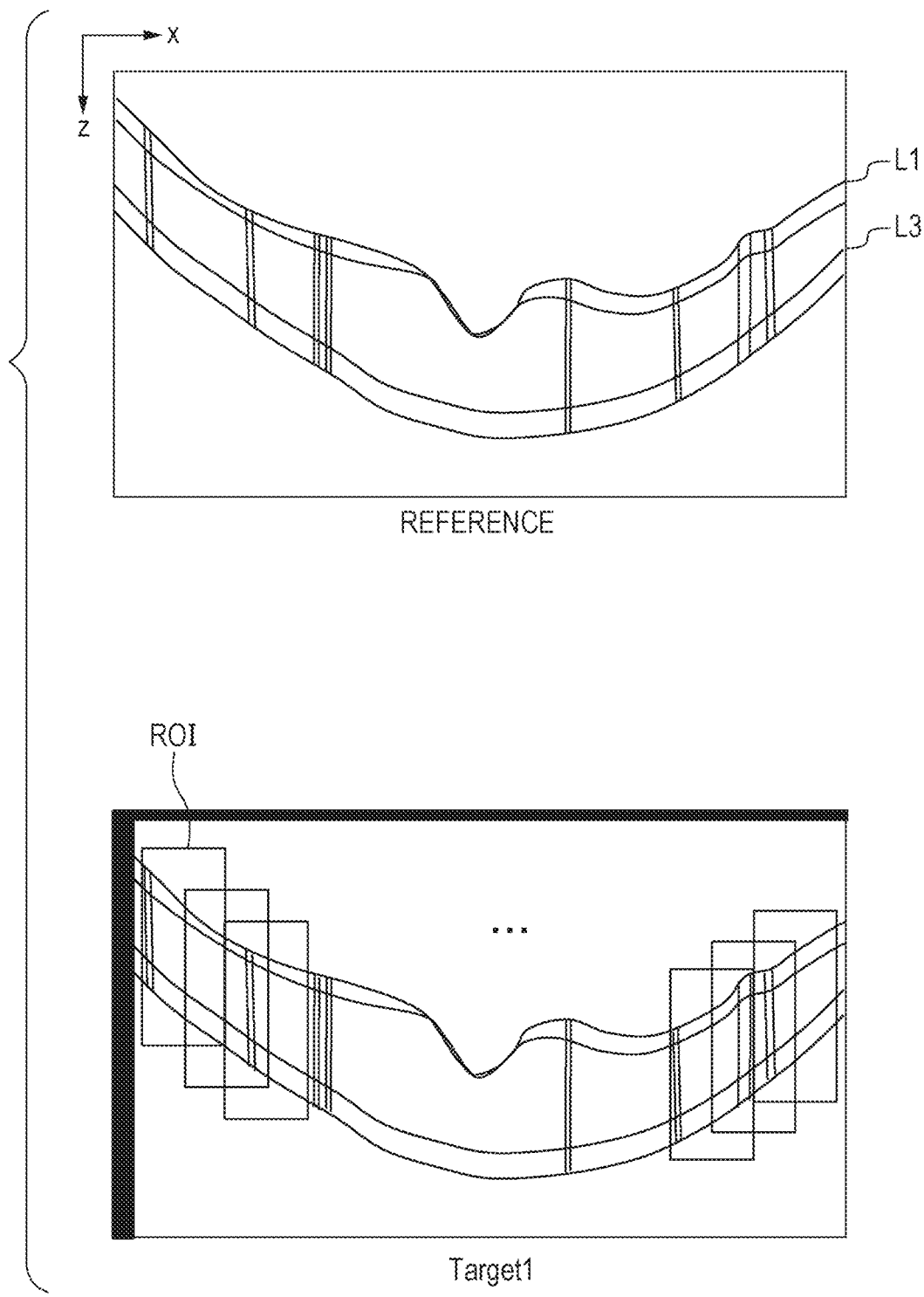
FIG. 14 is a diagram for explaining an example of fourth alignment.

FIG. 13 illustrates 3D tomographic images of Data 0, Data 1, and Data 2, wherein the upper 3D tomographic images are yet-to-be-aligned images, that is, before alignment, and the lower 3D tomographic images are images deformed after the first alignment, the second alignment, and the third alignment. As illustrated herein, the 3D tomographic images after intra-data alignment and inter-data alignment have been aligned regarding X, Y, and Z of the retina between Data 0, Data 1, and Data 2.

<Step S3566>

In S3566, the third alignment unit 337 detects the difference between the reference data and the target data in Depth Map for which inter-data z alignment has been completed. Each position (x, y) where the absolute value of the difference is not less than a threshold is determined as a position of low alignment precision and is not used for overlaying. Therefore, zero is set as an invalid area in the Mask image of the target data.

<Step S357>

In S357, the fourth alignment unit 338 sets a plurality of areas for alignment between the reference data and the target data at characteristic portion inside a tomographic image, and performs processing for alignment in the horizontal direction (x axis) and the depth direction (z axis) of the retina for each area. The alignment performed in this step is described as local alignment in the z direction. With reference to the flowchart of FIG. 6, local alignment performed by the fourth alignment unit 338 will now be explained.

<Step S3571>

In S3571, the fourth alignment unit 338 acquires the boundary information that was detected in S351. In the present embodiment, it is assumed that the boundaries L1 and L3 are used for alignment in the depth direction.

<Step S3572>

In S3572, the fourth alignment unit 338 sets areas for alignment in such a way as to include characteristic portion of the target image. This processing will now be explained with reference to FIGS. 14A and 14B.

FIGS. 14A and 14B illustrate a tomographic image in a 3D tomographic image of reference data and a tomographic image in a 3D tomographic image of the target of alignment. In the example illustrated therein, a plurality of areas for alignment (ROI: Region of Interest) is set in the target image 1, which is the target of alignment, on the basis of the boundary information L1 and L3 of the tomographic image taken as the reference. The depth-directional size of ROI is set to be wider over and under L1 and L3 vertically by approximately a few tens of pixels each. When the parameters of being wider over and under them vertically by approximately a few tens of pixels are set, the parameters are, in some cases, corrected using the result of non-local big picture alignment. As shown in the target image 1 of FIG. 14B, in non-local big picture alignment, in a case where the entire image is shifted downward, an invalid area exists at the upper end portion of the image. In such a case, it is necessary to correct the default ROI size such that the ROI setting range and the search area thereof do not contain any invalid area. The horizontal ROI size is set on the basis of the image segmentation size. The number of the segments is set in accordance with imaging parameters such as the size of the image (the number of A scans) and imaging size of the image (3 mm). For example, in the present embodiment, assuming that the number of A scans is 300 and the imaging size is 3 mm, the number of the segments is 10. Correction is performed using the result of non-local big picture alignment for the horizontal size and the ROI setting value, too. Similarly to the parameters in the vertical direction, an invalid area could exist in the horizontal direction, too. Therefore, it is necessary to configure settings such that the ROI setting range and the search area thereof do not contain any invalid area.

The pieces of ROI for local alignment are set in such a way as to overlap with one another. This is because, if the ROI size is set to be small without any ROI overlap, there is a possibility that some pieces of ROI might not contain any characteristic portion. For example, if the retina is imaged with a narrow angle of view, in some case, a flat tissue is pictured in a wide area in the image. On the other hand, if the range of ROI is set to be wide such that characteristic portion will be included without any ROI overlap, the number of samplings for local alignment will be small, resulting in rough alignment. Therefore, in order to solve these problems, the x-directional ROI size is set to be large, and the pieces of ROI are set in such a way as to overlap with one another. In FIG. 14B, although no ROI is shown at the center area of the image, actually, the pieces of ROI are set on the retina from the left end to the right end of the image. Moreover, ideally, it is better to set the ROI pitch while taking, into consideration, the range of search conducted when ROI alignment is performed. Specifically, if the range of search in the horizontal direction during ROI alignment is defined as XR, it is set such that the interval between the center coordinates of adjacent pieces of ROI is not less than 2×R. This is because there is a possibility that the center positions of adjacent pieces of ROI might be replaced with each other if the interval between the center coordinates thereof is less than 2×R.

<Step S3573>

In S3573, the fourth alignment unit 338 performs area alignment using the ROI. The area alignment is performed between tomographic images. Therefore, alignment in accordance with the degree of image similarity is performed using Formula 1 similarly to OCTA image alignment described earlier in S3534. However, the value for evaluating the degree of similarity is not limited to this example. SSD (Sum of Squared Difference) or SAD (Sum of Absolute Difference) may be used instead. Alternatively, POC (Phase Only Correlation) may be used for alignment.

Image alignment involves searching for the place where the ROI set on the target image is located on the tomographic image taken as the reference. When this location search is carried out, because of 3D tomographic image data deformation done using the results of the first alignment, the second alignment, and the third alignment, the position on the reference image and the position on the target image approximately match. Because of this approximate match, regarding the range of search for alignment on the reference image, it suffices to search within an area of several to a few tens of pixels vertically and horizontally from the initial ROI position, and the place of the greatest resemblance is adopted as the alignment result. The search area may be fixed, or variable depending on the imaging angle of view, the region to be imaged, and/or the position of the image (end or the center). The amount of eye movement during the capturing of one image is small in a case where the imaging angle of view is narrow and the speed of scan is high. The amount of eye movement increases as the imaging angle of view becomes wider. Therefore, a wider range of search may be set for a wider imaging angle of view. The amount of eye movement at a peripheral portion is larger than the amount of eye movement at the center of eye rotation. Therefore, a wider range of search may be set for the peripheral portion.

<Step S3574>

Figure 15A:
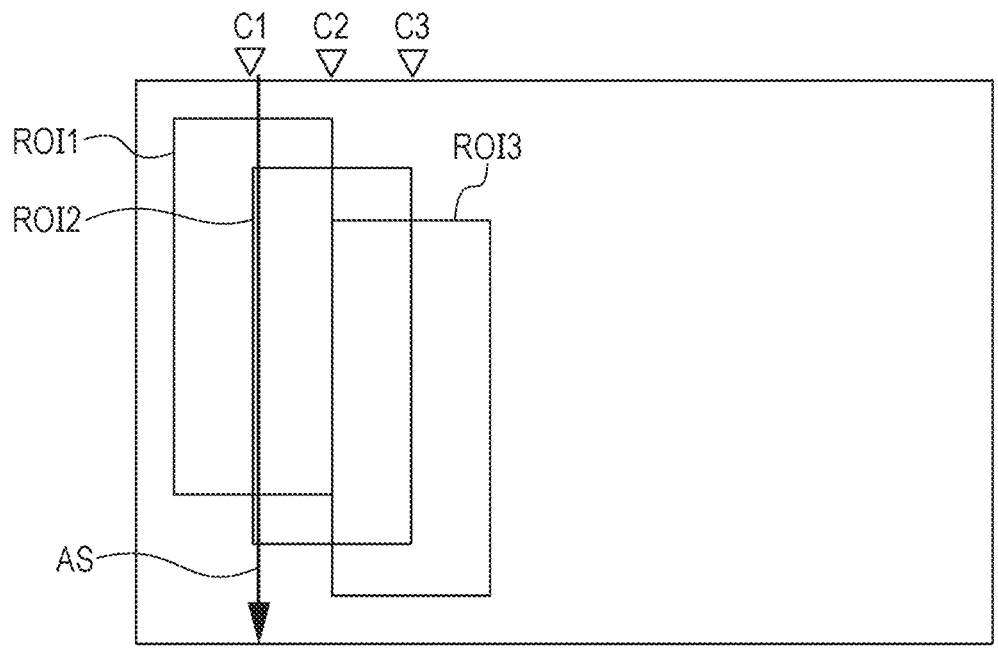
FIG. 15A is a diagram that illustrates an example of initially-set areas of ROI in fourth alignment.
Figure 15B:
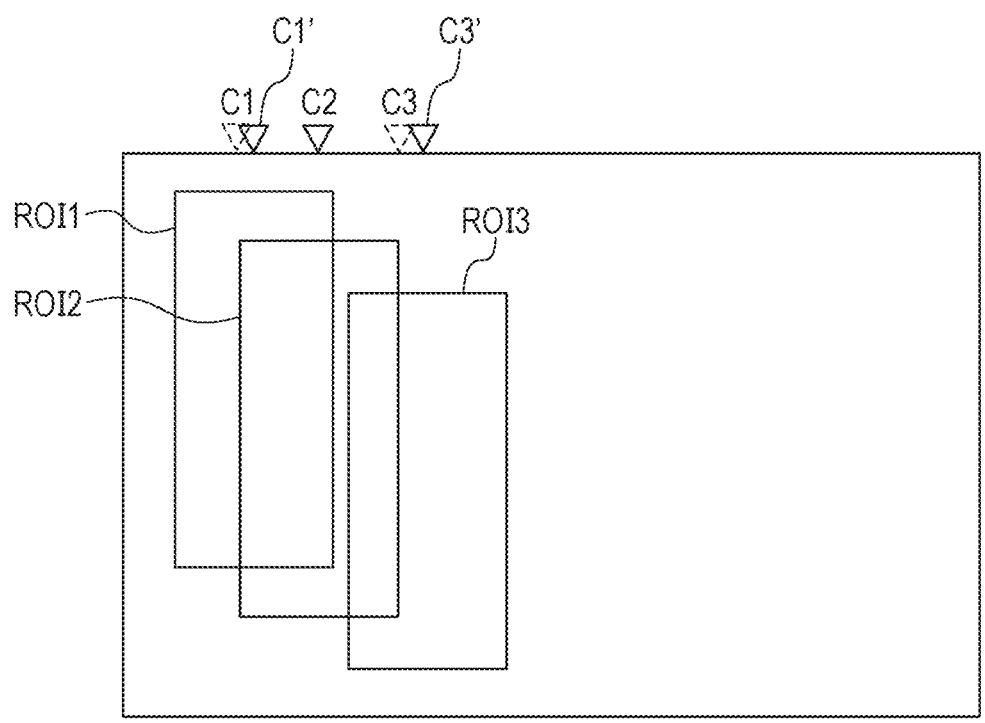
FIG. 15B is a diagram that illustrates an example of ROI movement.

In S3574, the fourth alignment unit 338 calculates the amount of movement of each A scan by interpolating the alignment parameters obtained in S3573. This processing will now be explained with reference to FIGS. 15A and 15B. FIG. 15A shows the initially-set areas of ROI 1, ROI 2, and ROI 3. Downward triangles C1, C2, and C3 represent the center of ROI 1, ROI 2, and ROI 3 respectively. FIG. 15B shows an example of ROI movement after the alignment in S3573. In the example illustrated in FIG. 15B, ROI 1 and ROI 3 move to the right, and ROI 2 does not move.

Therefore, the center C1 of ROI 1 and the center C3 of ROI 3 move to C1' and C3' respectively. The amount of movement of A scan is calculated from the amount of movement of each ROI. Specifically, the calculation is performed on the basis of the amount of shifting of the center positions of two ROIs that are adjacent to each other. For example, the center position of ROI 1 shifts from C1 to C1', whereas the center position of ROI 2 remains the same at C2. Formulae 12, 13, and 14 for calculating the amount of x-directional movement of each A scan between C1 and C2 before deformation are shown below.

$$W = 1.0 - \frac{(A\_before - X1)}{(X2 - X1)} \quad (12)$$

$$TransX = \Delta X1 * W + \Delta X2 * (1.0 - W) \quad (13)$$

$$A\_after = A\_before - TransX \quad (14)$$

In Formulae 12, 13, and 14, X1, X2 denotes the initial center coordinate of each ROI; ΔX1, ΔX2 denotes the amount of x-directional movement of the center coordinate of each ROI; $A\_before$ denotes the value of A scan index before deformation; $A\_after$ denotes the value of A scan index after deformation, referred to by $A\_before$. For example, if $A\_before$ is 55 and if $A\_after$ as a result of calculation is 56, A scan data of A scan index 56 is substituted into A scan index 55. On the basis of the same concept as that of Formulae 12, 13, and 14, it is possible to calculate the z-directional movement amount from the amount of movement of the center of each ROI, and data is moved by several pixels in the vertical direction. The value of $A\_after$ may be a real number or an integer. If it is a real number, new A scan data is generated from pieces of A scan data by using an interpolation method (Bilinear, Bicubic, etc.). If it is an integer, the data of the corresponding A scan index is referred to as it is. Although an example of performing alignment locally both in the x direction and the z direction is described above, the scope of the disclosure is not limited to this example. For example, deformation may be performed locally in only either one of the x direction and the z direction. Since alignment is done in the x direction by tracking at the time of imaging, for the purpose of reducing the processing load, local alignment in the z direction only may be performed.

<Step S3575>

In S3575, the fourth alignment unit 338 performs movement in the x direction and the z direction for each A scan on the basis the A scan movement amount calculated in S3574. By this means, it is possible to generate a tomographic image deformed in the unit of A scan. Both the 3D data tomographic image data and the 3D motion contrast data are deformed.

<Step S3576>

In S3576, it is determined whether or not, for every tomographic image of the 3D data taken as the reference, local alignment has been done for all pieces of the alignment target data. If the processing has not been done for all pieces of the data yet, the process returns to S3561. The local alignment ends if all pieces of the data have been locally aligned.

Local alignment is performed through these processing steps. Referring back to the processing flow in FIG. 3B, the next step will now be explained.

<Step S358>

In S358, the image synthesis unit 339 adds the reference 3D motion contrast data selected by the selection unit 335 and pieces of 3D motion contrast data together, and calculates the average of them. For the averaging processing, the sum SUM_A of values obtained by multiplying the values of pieces of motion contrast data by the Mask image, on a voxel-by-voxel basis, and the sum SUM_B of the values of the Mask image are pre-stored respectively. The values of the Mask image contain zero set as an invalid area for artifact removal and set as an invalid area with data absence due to alignment. Therefore, values that differ from voxel to voxel are held in the sum SUM_B of the values of the Mask image. Under normal circumstances, movement by several tens of voxels in x, y, and z in alignment is anticipated. Therefore, if the number of pieces of data used for overlaying one on another is N, the voxel values of SUM_B near the center of the image are N, whereas the voxel values of SUM_B at an end portion of the image are less than N. In the averaging processing, it is possible to obtain motion contrast data with averaging calculation by dividing SUM_A by SUM_B.

Figure 16A:
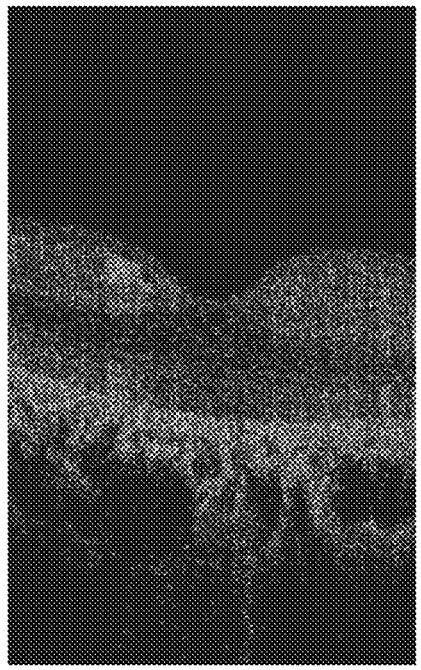
FIG. 16A is a diagram that illustrates an example of three-dimensional motion contrast data before averaging.
Figure 16B:
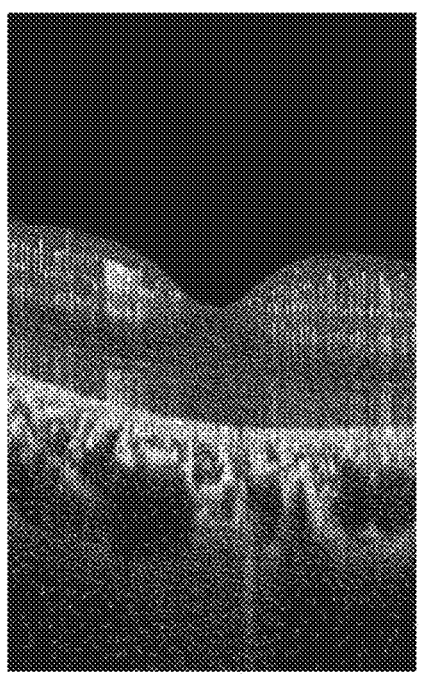
FIG. 16B is a diagram that illustrates an example of three-dimensional motion contrast data after averaging.
Figure 17A:
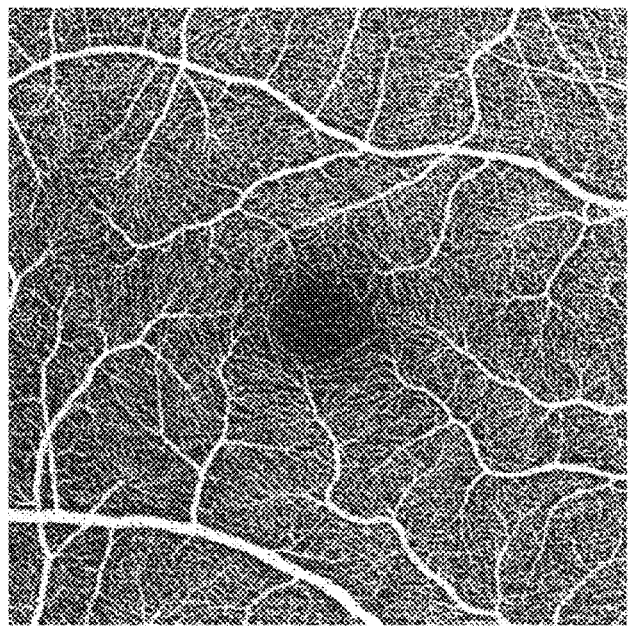
FIG. 17A is a diagram that illustrates an example of a retinal-surface OCTA image generated from 3D motion contrast data before averaging.
Figure 17B:
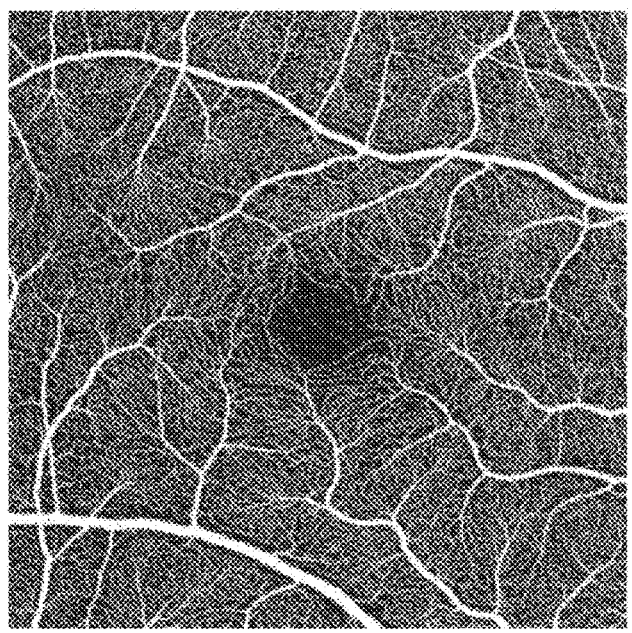
FIG. 17B is a diagram that illustrates an example of a retinal-surface OCTA image generated from 3D motion contrast data after averaging.
Figure 18A:
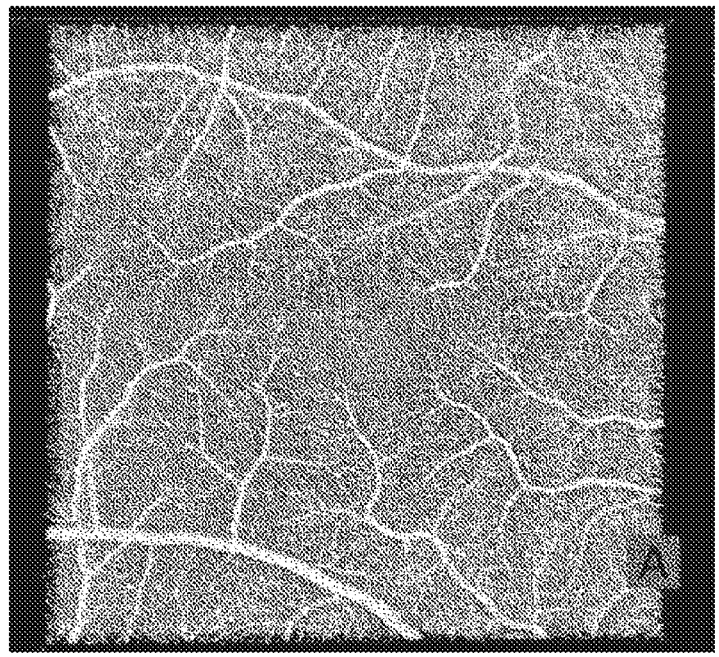
FIG. 18A is a diagram that illustrates an example of volume-rendered 3D motion contrast data before averaging.
Figure 18B:
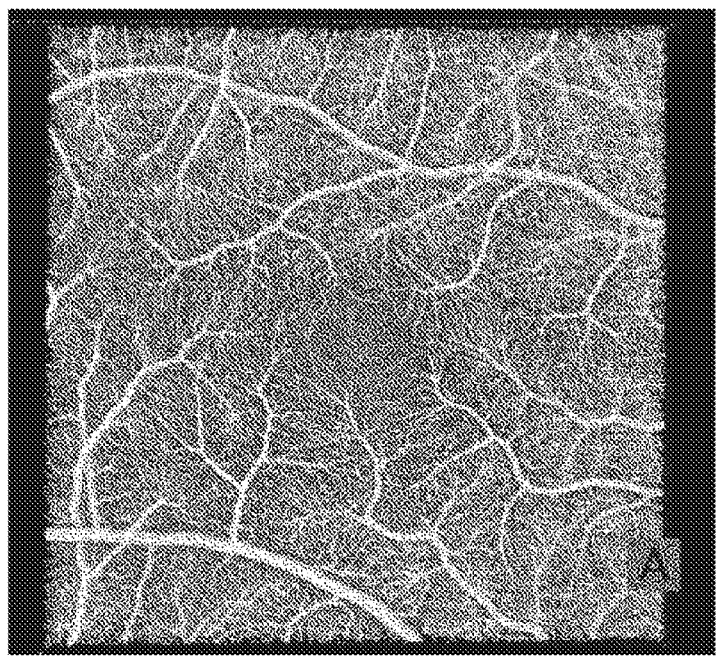
FIG. 18B is a diagram that illustrates an example of volume-rendered 3D motion contrast data after averaging.

An example of motion contrast data before and after the averaging processing described above will now be shown with reference to FIGS. 16A and 16B depicting the x-z plane, accompanied by an example of an OCTA image in FIGS. 17A and 17B and an example of volume rendering of 3D motion contrast data in FIGS. 18A and 18B.

More specifically, an example of the x-z plane of 3D motion contrast data before the averaging processing is illustrated in FIG. 16A, and an example of the x-z plane of 3D motion contrast data after the averaging processing is illustrated in FIG. 16B. An example of a retinal-surface OCTA image generated from 3D motion contrast data before the averaging processing is illustrated in FIG. 17A, and an example of a retinal-surface OCTA image generated from 3D motion contrast data after the averaging processing is illustrated in FIG. 17B. An example of volume-rendered 3D motion contrast data before the averaging processing is illustrated in FIG. 18A, and an example of volume-rendered 3D motion contrast data after the averaging processing is illustrated in FIG. 18B. As illustrated in FIGS. 16A and 16B to 18A and 18B, it is possible to obtain 3D motion contrast data with enhanced contrast by performing the averaging processing described above. If volume rendering of motion contrast data is performed as illustrated in FIGS. 18A and 18B, it becomes easier to understand the upper/lower relation in the depth direction of a blood vessel, which is difficult to recognize on a 2D OCTA image.

Similar averaging processing is performed for pieces of 3D tomographic image data as done for the 3D motion contrast data.

<Step S359>

In S359, on the basis of the input 3D motion contrast data and the input 3D tomographic image data that were stored in S3561 and on the basis of the movement amount in the depth direction of each A scan that was stored in S3563, the third alignment unit 337 returns the retinal position of the reference data (in the present embodiment, Data 1) to the input depth position. Specifically, the 3D motion contrast data and the 3D tomographic image data after the averaging processing in S358 are returned to the original state by using the movement amount in the depth direction of each A scan that was stored in S3563 For example, if a certain A scan was moved down by 5, it is moved up by 5 in this step. Moving up by 5 produces an invalid area at the bottom portion of the data. Therefore, data of the same coordinate position in the input 3D motion contrast data and the input 3D tomographic image data that were stored in S3561 are respectively copied into the invalid area.

Although an example of copying the input data to the invalid area of the data after the averaging processing is described above, the scope of the disclosure is not limited to this example. Data in a range corresponding to the original coordinate position for the input 3D data that were stored by the third alignment unit 337 may be extracted from the 3D data after the averaging processing and may be then copied. By this means, it is possible to reduce the processing to one copying step only, whereas the processing described above requires two steps, that is, copying to the invalid area after data movement. Therefore, it is possible to reduce the processing load. In this case, since the copying is performed for the input 3D data that were stored by the third alignment unit 337, final output data will be the data stored by the third alignment unit 337.

After completion of these processing steps, the process returns to the flowchart of FIG. 3A.

<Step S306>

In S306, high-quality 3D motion contrast data or high-quality 3D tomographic image data generated as the result of processing including averaging is displayed on the display unit 600.

An OCTA image is generated by projecting, onto a 2D plane, motion contrast data corresponding to a generation range between upper and lower limits specified for the 3D motion contrast data after the averaging processing, and the generated OCTA image is displayed. Alternatively, color settings are applied to threshold-processed 3D motion contrast data, and superimposed display on 3D tomographic image data containing luminance values is performed. Such display makes it possible to easily understand correspondences between the retinal structure and the locations of motion contrast occurrence. Alternatively, volume rendering may be performed on the 3D motion contrast data after the averaging processing, and the volume-rendered data may be displayed three-dimensionally.

<Step S307>

In S307, a non-illustrated instruction acquisition unit acquires, from the outside, instructions as to whether to terminate the tomographic image capturing by the image processing system 100 or not. The instructions are inputted by an operator by means of the input unit 700. If the instructions for terminating the processing are acquired, the image processing system 100 terminates the processing. In a case where the image capturing should be continued without terminating the processing, the process returns to S302, and the image capturing continues. The processing of the image processing system 100 is performed as explained above.

With the configuration described above, in the present embodiment, alignment of pieces of motion contrast data is performed, and artifact area removal and image synthesis are performed. Therefore, it is possible to acquire high-quality 3D motion contrast data even in a case where artifacts exist in motion contrast data.

More specifically, in the present embodiment, non-local big picture alignment is performed using boundaries and image feature quantity, and reference selection and additive area selection are performed. In the depth direction, intra-image-data alignment and inter-image-data alignment in terms of retinal depth and slope are performed. Moreover, in a 2D tomographic image in an aligned 3D tomographic image, the degree of similarity between regions is calculated using the corresponding local regions, and alignment is performed on a region-by-region basis. Because of these processes, even in a case where local retinal layer deformation exists due to artifacts occurring during imaging or due to involuntary eye movements during fixation, etc., it is possible to generate 3D motion contrast data with high quality.

Variation Example 1

In an example of the present embodiment, the data of N-times-repeated imaging is captured by imaging the same imaging range using the same scan pattern. However, the scope of the disclosure is not limited to this example. For example, data captured by imaging a range of 3 mm×3 mm by 300×300 (main scan×sub scan) and data captured by imaging a range of 3 mm×3 mm by 600×600 may be aligned with each other. The same size in the depth direction, for example, 1,000, is set for both of these pieces of data. In this case, the alignment processing described above is performed after performing data conversion processing for matching the physical size per voxel of the two. For example, the processing may be performed after enlarging the data of 300×300 to 600×600 by interpolation. Alternatively, the processing may be performed after reducing the data of 600×600 to 300×300 by interpolation. In a case where data captured by imaging a range of 3 mm×3 mm by 300×300 and data captured by imaging a range of 6 mm×6 mm by 600×600 are aligned with each other, the alignment processing is performed without any size change because the physical size per voxel of the two is the same. By this means, it is possible to perform averaging processing for pieces of data based on different imaging ranges and/or different scan densities.

Variation Example 2

In an example of the present embodiment, an image evaluation value, an alignment parameter evaluation value, and an artifact area evaluation value are used in the selection of a reference image. However, the scope of the disclosure is not limited to this example. For example, a layer detection evaluation value may be additionally used in the selection of a reference image.

The layer detection evaluation value is calculated when the detection unit 333 performs layer detection. The luminance value of a tomographic image is referred to for each A scan when layer detection is performed, wherein the reliability of detection precision may be set and determined for each A scan on the basis of information on the luminance value of the tomographic image at the time of detection. For example, since there is a possibility of failure in detecting the retina accurately due to blinking, etc. in a case where the luminance of a tomographic image is low, the reliability of detection is defined as low. Alternatively, the definition may be based on not only the luminance value but also the boundary position. For example, the reliability of detection is low because of the possibility of failure in detecting the layer accurately if the boundary adjoins the upper end or the lower end in the Z direction.

With the use of the reliability of layer detection described above, the layer detection area not less than a threshold is evaluated. The same method as that used for the artifact area evaluation value in Formula 7 can be used for evaluating the layer detection area. For example, it is possible to do so by replacing the non-artifact area expressed by T (x, y) in Formula 7 with the layer detection area not less than a threshold. By this means, since the depth information of tomographic data is also used, it is possible to select a more reliable piece of data as the reference image.

Variation Example 3

In an example of the present embodiment, the initial reference data is taken at the center boundary of the data in intra-data z-directional alignment. However, the scope of the disclosure is not limited to this example. For example, the initial reference data may be taken at the location where the reliability of layer detection of the boundary L1 is high near the center of the image. As shown in Variation Example 2 above, the reliability of layer detection is defined depending on the brightness level of the image and/or the z-directional position of the layer boundary. According to this modification, the alignment starts on the basis of the position of high reliability. Therefore, a reduction in alignment error can be expected.

Variation Example 4

In an example of the present embodiment, both 3D motion contrast data and 3D tomographic image data are deformed three-dimensionally and averaged. However, the scope of the disclosure is not limited to this example. The motion contrast data only may be deformed. In this case, the fourth alignment unit 338 performs alignment using the motion contrast data, although tomographic images are used for alignment in the present embodiment. The averaging processing by the image synthesis unit 339 is also performed for the 3D motion contrast data only. If it is sufficient to ensure high image quality for motion contrast data only, the motion contrast data only is deformed. Therefore, it is possible to reduce the processing load.

Variation Example 5

In an example of the present embodiment, alignment is performed with OCTA image enlargement on the x-y plane in S3534, and movement parameters on the x-y plane are converted into movement parameters corresponding to the original size in S3565. Then, 3D data shape deformation is performed on the basis of the original size. However, the scope of the disclosure is not limited to this example. For example, the 3D data itself may be enlarged to perform alignment, and outputting may be performed in this state without reverse size conversion. Specifically, assuming that 3D data size is 300×300×1,000 (main scan×sub scan× depth), the data may be enlarged to 600×600×1,000 to perform alignment and averaging, and the processed data may be outputted in this size without reverse conversion. Alternatively, after enlargement to 600×600×1,000 and subsequent alignment and averaging, the size of the processed data may be finally returned to the size of 300×300×1,000 before outputting. By this means, further enhancement in the image quality of the output 3D data after the averaging can be expected.

Variation Example 6

In an example of the present embodiment, the third alignment unit 337 performs processing of returning the data moved in the z direction to the input z position in S359. However, the scope of the disclosure is not limited to this example. For example, the result of z alignment performed by the third alignment unit 337 may be outputted without returning the z-moved data to the input z position. By this means, it is possible to display data aligned in terms of depth and slope in the z direction. In this case, it is unnecessary to perform processing of storing reference data in S3561. Instead, since the data as a whole has been deformed in the z direction, the z-directional position of the layer boundary detected by the detection unit 333 is corrected on the basis of the movement amount stored in S3563.

Variation Example 7

In the present embodiment, processing from imaging to display is described and illustrated as a sequential process flow. However, the scope of the disclosure is not limited thereto. For example, high-quality image generation processing may be performed using image data that has already been captured. In this case, processing regarding imaging is skipped, and pieces of "already-captured" 3D motion contrast data and pieces of already-captured 3D tomographic image data are acquired instead. Then, in S305, high-quality image generation processing is performed. By this means, for data captured by performing imaging more than once, it is possible to perform high-quality image generation processing when needed, without any need for processing at the time of imaging. Therefore, a user is able to concentrate the user's mind on taking photos at the time of imaging.

Other Embodiments

Embodiment of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment and/or controlling the one or more circuits to perform the functions of one or more of the above-described embodiment. The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2017-172335, filed Sep. 7, 2017, which is hereby incorporated by reference herein in its entirety.

What is claimed is:

1. An image processing apparatus, comprising:
   a first planar alignment unit configured to perform first planar alignment including alignment between pieces of three-dimensional data of a subject eye in a plane orthogonal to a depth direction of the subject eye, the pieces of three-dimensional data being obtained at different times, the three-dimensional data including pieces of two-dimensional data obtained at different positions;

a first depth alignment unit configured to perform first depth alignment including alignment between pieces of two-dimensional data in at least one piece of three-dimensional data among the pieces of three-dimensional data and further including alignment between pieces of three-dimensional data in the depth direction; and a generation unit configured to generate interpolation data of at least one piece of three-dimensional data among the pieces of three-dimensional data by using a result of the first planar alignment and a result of the first depth alignment.

2. The image processing apparatus according to claim 1, further comprising: an image generation unit configured to generate new three-dimensional data by using the pieces of three-dimensional data and the interpolation data.

3. The image processing apparatus according to claim 1, wherein the first planar alignment unit performs the first planar alignment by using an En-face image of the subject eye generated from at least a part of a piece of the three-dimensional data in the depth direction, and wherein the first depth alignment is performed after the first planar alignment.

4. The image processing apparatus according to claim 3, further comprising: a selection unit configured to select, from among the pieces of three-dimensional data, a piece of three-dimensional data to be taken as a reference for the alignment between the pieces of three-dimensional data by using at least one of an evaluation value regarding the En-face image, an evaluation value regarding the first planar alignment, an evaluation value regarding an artifact of the En-face image, and an evaluation value regarding layer detection of the pieces of three-dimensional data.

5. The image processing apparatus according to claim 4, further comprising: a second planar alignment unit configured to perform second planar alignment for each main scan line of the En-face mage corresponding to other three-dimensional data in relation to the En-face image corresponding to the piece of three-dimensional data taken as the reference in a direction of a main scan.

6. The image processing apparatus according to claim 5, wherein, in the second planar alignment, an artifact area in the other three-dimensional data is detected by using a degree of similarity calculated for each main scan line, and the detected artifact area is not used for generating new three-dimensional data.

7. The image processing apparatus according to claim 3, wherein the first planar alignment unit performs the first planar alignment including alignment regarding rotation of the subject eye by using the En-face image.

8. The image processing apparatus according to claim 1, further comprising: a determination unit configured to determine, by using a degree of similarity of at least a part of other three-dimensional data to three-dimensional data taken as a reference for the alignment between the pieces of three-dimensional data, whether to use at least a part of data for generating new three-dimensional data or not.

9. The image processing apparatus according to claim 1, further comprising: a second depth alignment unit configured to perform second depth alignment between pieces of interpolation data in the depth direction in a case where the pieces of interpolation data are generated for the pieces of three-dimensional data and configured to perform, in a case where no interpolation data is generated for at least one of the pieces of three-dimensional data, second depth alignment between the three-dimensional data and the interpolation data in the depth direction.

10. The image processing apparatus according to claim 9, wherein the second depth alignment unit performs the second depth alignment for each A scan.

11. The image processing apparatus according to claim 1, wherein the three-dimensional data includes three-dimensional tomographic data of luminance or three-dimensional motion contrast data.

12. The image processing apparatus according to claim 11,
wherein the three-dimensional data is the three-dimensional motion contrast data, wherein the first planar alignment unit performs the first planar alignment by using an En-face image of the subject eye generated from at least a part of the three-dimensional motion contrast data in the depth direction, and
wherein the first depth alignment unit performs the first depth alignment including alignment regarding slope between the pieces of two-dimensional data arranged along a direction of sub scan by using a layer detection result of three-dimensional tomographic data of luminance corresponding to the three-dimensional motion contrast data.

13. The image processing apparatus according to claim 1, wherein the pieces of three-dimensional data are data obtained using a scan method based on the same direction of main scan.

14. An image processing method, comprising:
performing first planar alignment including alignment between pieces of three-dimensional data of a subject eye in a plane orthogonal to a depth direction of the subject eye, the pieces of three-dimensional data being obtained at different times, the three-dimensional data including pieces of two-dimensional data obtained at different positions;
performing first depth alignment including alignment between pieces of two-dimensional data in at least one piece of three-dimensional data among the pieces of three-dimensional data and further including alignment between pieces of three-dimensional data in the depth direction; and
generating interpolation data of at least one piece of three-dimensional data among the pieces of three-dimensional data by using a result of the first planar alignment and a result of the first depth alignment.

15. A non-transitory computer-readable storage medium storing a program for causing a computer to execute the method according to claim 14.

* * * * *